US006884787B2

(12) United States Patent
Monia et al.

(10) Patent No.: US 6,884,787 B2
(45) Date of Patent: Apr. 26, 2005

(54) ANTISENSE MODULATION OF TRANSFORMING GROWTH FACTOR-BETA 3 EXPRESSION

(75) Inventors: Brett P. Monia, Encinitas, CA (US); Susan M. Freier, San Diego, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/906,158

(22) Filed: Jul. 14, 2001

(65) Prior Publication Data

US 2003/0078217 A1 Apr. 24, 2003

(51) Int. Cl.[7] .......................... A01N 43/04; A61K 31/70

(52) U.S. Cl. .............................. 514/44; 435/6; 435/325; 435/375; 536/23.1; 536/24.5

(58) Field of Search ................................ 514/44; 435/6, 435/325, 375; 536/23.1, 24.3, 24.32, 24.5

(56) References Cited

U.S. PATENT DOCUMENTS

| | | | | | |
|---|---|---|---|---|---|
| 5,214,136 | A | * | 5/1993 | Lin et al. | 514/44 |
| 5,650,494 | A | * | 7/1997 | Cerletti et al. | 435/69.4 |
| 5,801,154 | A | * | 9/1998 | Baracchini et al. | 514/44 |
| 5,994,076 | A | * | 11/1999 | Chenchik et al. | 435/6 |
| 6,110,667 | A | * | 8/2000 | Lopez-Nieto et al. | 435/6 |

FOREIGN PATENT DOCUMENTS

| | | |
|---|---|---|
| WO | WO 94/25588 | 11/1994 |
| WO | WO 98/40747 | 9/1998 |
| WO | WO 99/63975 | 12/1999 |

OTHER PUBLICATIONS

Chai, Y et al. Developmental Biology (1994) 162:85–103.*
Liu, J. et al. Developmental Dynamics (2000) 217:343–360.*
Caniggia, I. et al. Journal of Clinical Investigation (1999) 103(12):1641–1650.*
Dijke, P.T. et al. Proc. Nat'l Acad. Sci. (1988)85:4715–4719.*
Yee, W. et al. Am. J. Phys. (1996) 270(14) L992–L1001.*
Braasch, D. A. Biochemistry. Apr. 2002; 41(14): 4503–4510.*
Branch, A. D., (1998). Trends Biochem Sci. Feb. 1998;23(2):45–50.*
Agrawal, S. Trends Biotechnol. Oct. 1996;14(10):376–87.*
Gerwirtz et al., Proc. Natl. Acad. Sci. v 93, pp. 3161–3163.*
Tamm, I. et al. The Lancet. Aug. 2001, 358: 489–497.*
Chai, Y et al. Developmental Biology (1994) 162:85–103.*
Liu, J. et al. Developmental Dynamics (2000) 217:343–360.*
Caniggia, I. et al. Journal of Clinical Investigation (1999) 103(12):1641–1650.*
Dijke, P.T. et al. Proc. Nat'l Acad. Sci. (1988)85:4715–4719.*
Yee, W. et al. Am. J. Phys. (1996) 270(14) L992–L1001.*
Duke et al., "Identification of another member of the transforming growth factors type β gene family", Proc. Natl. Acad. Sci. USA 1988 85:4715–4719.
Abou–Shady et al., *Transforming growth factor betas and their signaling receptors in human hepatocellular carcinoma, Am. J. Surg.,* 1999, 177:209–215.
Ardley et al., *Fine mapping of 12 previously unassigned EST clones to individual YACs in the familial Alzheimer's disease (FAD) region of chromosome 14q24.3, Cytogenet. Cell Genet.,* 1998, 82:107–109.
Caniggia et al., *Inhibition of TGF–beta 3 restores the invasive capability of extravillous trophoblasts in preeclamptic pregnancies, J. Clin. Invest.,* 1999, 103:1641–1650.
Chai et al., *Specific transforming growth factor–beta subtypes regulate embryonic mouse Meckel's cartilage and tooth development, Dev. Biol.,* 1994, 162:85–103.
Crowe et al., *Delayed wound healing in immunodeficient TGF–beta 1 knockout mice, J. Invest. Dermatol.,* 2000, 115:3–11.
Ghellal et al., *Prognostic significance of TGF beta 1 and TGF beta 3 in human breast carcinoma, Anticancer Res.,* 2000, 20:4413–4418.
Kaartinen et al., *Abnormal lung development and cleft palate in mice lacking TGF–beta 3 indicates defects of epithelial–mesenchymal interaction, Nat. Genet.,* 1995, 11:415–421.
Liu et al., *Transforming growth factor beta2, but not beta1 and beta3, is critical for early rat lung branching, Dev. Dyn.,* 2000, 217:343–360.
Markowitz, *Atherosclerosis, just another cancer?, J. Clin. Invest.,* 1997, 100:2143–2145.
Nakajima et al., *An Autocrine Function for Transforming Growth Factor (TGF) –b3 in the Tranformation of Atrioventricular Canal Endocardium into Mesenchyme during Chick Heart Development, Developmental Biology,* 1998, 194:99–113.
Pasche, *Role of tranforming growth factor beta in cancer, J. Cell Physiol.,* 2001, 186:153–168.
Piek et al., *Specificity, diversity, and regulation in TGF–beta superfamily signaling, Faseb J.,* 1999, 13:2105–2124.

(Continued)

*Primary Examiner*—John L. LeGuyader
*Assistant Examiner*—James Douglas Schultz
(74) *Attorney, Agent, or Firm*—Licata & Tyrrell P.C.

(57) ABSTRACT

Antisense compounds, compositions and methods are provided for modulating the expression of transforming growth factor-beta 3. The compositions comprise antisense compounds, particularly antisense oligonucleotides, targeted to nucleic acids encoding transforming growth factor-beta 3. Methods of using these compounds for modulation of transforming growth factor-beta 3 expression and for treatment of diseases associated with expression of transforming growth factor-beta 3 are provided.

12 Claims, No Drawings

OTHER PUBLICATIONS

Romitti et al., *Candidate genes for nonsyndromic cleft lip and palate and maternal cigarette smoking and alcohol consumption: evaluation of genotype–environment interactions from a population–based case–control study of orofacial clefts, Teratology,* 1999, 59:39–50.

Rosier et al., *The potential role of transorming growth factor beta in fracture healing, Clin. Orthop.,* 1998, S294–300.

Schuppan et al., *Fibrosis of liver, pancreas and intestine: common mechanisms and clear targets?, Acta Gastroenterol. Belg.,* 2000, 63:366–370.

ten Dijke et al., *Identification of another member of the transforming growth factor type beta gene family, Proc. Natl. Acad. Sci. U. S. A.,* 1988, 85:4715–4719.

Yee et al., *Glucocorticoid–induced tropoelastin expression is mediated via transforming growth factor–beta 3, Am. J. Physiol.,* 1996, 270:L992–1001.

* cited by examiner

ANTISENSE MODULATION OF TRANSFORMING GROWTH FACTOR-BETA 3 EXPRESSION

FIELD OF THE INVENTION

The present invention provides compositions and methods for modulating the expression of transforming growth factor-beta 3. In particular, this invention relates to compounds, particularly oligonucleotides, specifically hybridizable with nucleic acids encoding transforming growth factor-beta 3. Such compounds have been shown to modulate the expression of transforming growth factor-beta 3.

BACKGROUND OF THE INVENTION

The transforming growth factor beta (TGF-β) superfamily of cytokines regulates a diverse array of physiologic functions including cell proliferation and growth, cell migration, differentiation, development, production of extracellular matrix, and the immune response. Each subgroup of this superfamily initiates a unique intracellular signaling cascade activated by ligand-induced formation and activation of specific serine/threonine kinase receptor complexes. In mammals, the TGF-β subfamily comprises three transforming growth factor beta isoforms, TGF-β1, TGF-β2, and TGF-β3. Signal transduction occurs through a requisite interaction between TGF-β type I and II receptors. Once transforming growth factor-beta 3 (also known as TGF-β3, TGF-beta-3, Tgfb3, and TGFB3) complexes with the type I and II TGF-β receptors, a phosphorylation cascade is initiated and sent to cytoplasmic effector molecules, the Smad proteins, for propagation of the kinase signal to nuclear transcription factors (Piek et al., *Faseb J.*, 1999, 13, 2105–2124).

Transforming growth factor-beta 3 was cloned from the human A673 rhabdomyosarcoma cell line (ten Dijke et al., *Proc. Natl. Acad. Sci. U.S.A.*, 1988, 85, 4715–4719) and mapped to the 14q24 locus, a region associated with familial Alzheimer's disease (FAD) (Ardley et al., *Cytogenet. Cell Genet.*, 1998, 82, 107–109.).

Transforming growth factor-beta 3 is believed to have a role in healing of wounds and bone fractures, and is not expressed in healthy skin. It can function as a morphogen when injected subperiosteally, inducing cartilage and bone formation (Rosier et al., *Clin. Orthop.*, 1998, S294–300). The expression pattern of transforming growth factor-beta 3 differs from that of the other TGF-β isoforms, which are believed to play distinct and nonredundant functions in wound healing. Upon wounding, expression of transforming growth factor-beta 3 is upregulated. However, in the absence of TGF-β1, transforming growth factor-beta 3 expression is delayed, leading to delayed wound healing (Crowe et al., *J. Invest. Dermatol.*, 2000, 115, 3–11).

Transforming growth factor-beta 3 also appears to play a role in orofacial and lung development, as allelic variants have been linked to the occurrence of cleft lip and palate in mice and humans (Kaartinen et al., *Nat. Genet.*, 1995, 11, 415–421; Romitti et al., *Teratology,* 1999, 59, 39–50). A transforming growth factor-beta 3 null mouse has been generated and homozygous Tgfb3 (–/–) mice have an incompletely penetrant cleft palate and a delay in pulmonary development, implicating transforming growth factor-beta 3 in defective palatogenesis and lung morphogenesis and suggesting involvement of this cytokine in epithelial-mesenchymal interaction (Kaartinen et al., *Nat. Genet.*, 1995, 11, 415–421).

A failure to downregulate the expression of transforming growth factor-beta 3 at 9-weeks gestation is believed to predispose human pregnancies to preeclampsia, a condition which results from insufficient invasion of the maternal decidua by placental extravillous trophoblasts (Caniggia et al., *J. Clin. Invest.*, 1999, 103, 1641–1650).

Mutant function or overactivity of TGF-β signaling components have been implicated in cancers of the colon, esophagus, pancreas, lung, and breast, as well as in hyperproliferative disorders of the kidney, atherosclerosis, and rheumatoid arthritis (Markowitz, *J. Clin. Invest.*, 1997, 100, 2143–2145; Pasche, *J. Cell Physiol.*, 2001, 186, 153–168; Piek et al., *Faseb J.*, 1999, 13, 2105–2124; Schuppan et al., *Acta Gastroenterol. Belg.*, 2000, 63, 366–370). Specifically, upregulation of transforming growth factor-beta 3 expression has been demonstrated in hepatocellular carcinoma cells and perineoplastic stroma of the liver, suggesting a role in tumor progression (Abou-Shady et al., *Am. J. Surg.*, 1999, 177, 209–215). Furthermore, increased expression of transforming growth factor-beta 3 in breast cancer patients is a prognostic indicator inversely correlated with survival (Ghellal et al., *Anticancer Res.*, 2000, 20, 4413–4418).

Chronic diseases of the liver, pancreas, intestine, kidneys, skin, and lungs often lead to organ fibrosis and scarring, and progressive loss of organ function, despite the use of antiviral or anti-inflammatory agents. TGF-βs are considered to be the most potent fibrogenic cytokines, and thus, the modulation of transforming growth factor-beta 3 activity and/or expression is an ideal target for therapeutic intervention in the prevention and treatment of fibroproliferative diseases (Schuppan et al., *Acta Gastroenterol. Belg.*, 2000, 63, 366–370).

Investigative strategies aimed at modulating expression of transforming growth factor-beta 3 and studying its function have involved the use of polyclonal antibodies and antisense oligonucleotides.

A phosphorothioate antisense oligodeoxynucleotide, 17 nucleotides in length, spanning the initiation codon of chicken transforming growth factor-beta 3 mRNA was used to show that transforming growth factor-beta 3 functions in an autocrine fashion in the atrioventricular canal endocardium during chick heart development (Nakajima et al., *Developmental Biology*, 1998, 194, 99–113).

One antisense oligonucleotide, 16 nucleotides in length, hybridizing to four codons 5' to the initiation site and including the initiation codon of the mouse transforming growth factor-beta 3 mRNA sequence, was used to show that transforming growth factor-beta 3 regulates embryonic Meckel's cartilage and tooth development (Chai et al., *Dev. Biol.*, 1994, 162, 85–103), and that transforming growth factor-beta 3 is induced by glucocorticoids in fetal rat lung fibroblasts (Yee et al., *Am. J. Physiol.*, 1996, 270, L992–1001) but does not inhibit rat lung branching in vitro (Liu et al., *Dev. Dyn.*, 2000, 217, 343–360).

Finally, this same antisense oligonucleotide was also used to show that inhibition of transforming growth factor-beta 3 restores the invasive capability of human trophoblasts into the maternal decidua in preeclamptic pregnancies (Caniggia et al., *J. Clin. Invest.*, 1999, 103, 1641–1650).

Disclosed and claimed in PCT Publication WO 94/25588 are phosphorothioate antisense oligonucleotides wherein said oligonucleotides hybridize with an area of a gene coding for transforming growth factor-beta 3 (Schlingensiepen et al., 1994).

Disclosed and claimed in PCT Publication WO 99/63975 are medicaments comprising a combination of at least one inhibitor of TGF-β family members and their receptors, wherein the inhibitor is an antisense nucleotide and/or ribozyme, as well as methods of using said medicaments in the treatment of neoplasms or infectious diseases (Schlingensiepen et al., 1999).

Disclosed and claimed in PCT Publication WO 98/40747 are methods for regulating or increasing trophoblast invasion in a subject comprising administration of therapeutically effective amounts of an inhibitor of transforming growth factor-beta 3 wherein the inhibitor is antisense to transforming growth factor-beta 3 (Caniggia et al., 1998).

Currently, there are no known therapeutic agents that effectively inhibit the synthesis of transforming growth factor-beta 3. Consequently, there remains a long felt need for additional agents capable of effectively inhibiting transforming growth factor-beta 3 function.

Antisense technology is emerging as an effective means for reducing the expression of specific gene products and therefore may prove to be uniquely useful in a number of therapeutic, diagnostic, and research applications for the modulation of transforming growth factor-beta 3 expression.

The present invention provides compositions and methods for modulating transforming growth factor-beta 3 expression, including modulation of the truncated mutants and the alternatively spliced isoforms of transforming growth factor-beta 3.

SUMMARY OF THE INVENTION

The present invention is directed to compounds, particularly antisense oligonucleotides, which are targeted to a nucleic acid encoding transforming growth factor-beta 3, and which modulate the expression of transforming growth factor-beta 3. Pharmaceutical and other compositions comprising the compounds of the invention are also provided. Further provided are methods of modulating the expression of transforming growth factor-beta 3 in cells or tissues comprising contacting said cells or tissues with one or more of the antisense compounds or compositions of the invention. Further provided are methods of treating an animal, particularly a human, suspected of having or being prone to a disease or condition associated with expression of transforming growth factor-beta 3 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding transforming growth factor-beta 3, ultimately modulating the amount of transforming growth factor-beta 3 produced. This is accomplished by providing antisense compounds which specifically hybridize with one or more nucleic acids encoding transforming growth factor-beta 3. As used herein, the terms "target nucleic acid" and "nucleic acid encoding transforming growth factor-beta 3" encompass DNA encoding transforming growth factor-beta 3, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of transforming growth factor-beta 3. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding transforming growth factor-beta 3. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding transforming growth factor-beta 3, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U. S. A.*, 2000, 97, 1976–81), protein arrays and proteomics (Celis, et al., *FEBS Lett.*, 2000, 480, 2–16; Jungblut, et al., *Electrophoresis,* 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O[, ]S[, ]or N-alkyl; O[, ]S[, ]or N-alkenyl; O[, ]S[ o]r N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b] [1,4]benzothiazin-2(3H)-one), G-clamps such as a substituted phenoxazine cytidine (e.g. 9-(2-aminoethoxy)-H-pyrimido[5,4-b] [1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94,/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci*., 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of transforming growth factor-beta 3 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding transforming growth factor-beta 3, enabling sandwich and other assays to easily be constructed to exploit this fact. Hybridization of the antisense oligonucleotides of the invention with a nucleic acid encoding transforming growth factor-beta 3 can be detected by means known in the art. Such means may include conjugation of an enzyme to the oligonucleotide, radiolabelling of the oligonucleotide or any other suitable detection means. Kits using such detection means for detecting the level of transforming growth factor-beta 3 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate,. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly (methylcyanoacrylate), poly (ethylcyanoacrylate), poly (butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 $\mu$m in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and triglycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci*., 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A*., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn*., 1980, 53, 2778) described liposomes comprising a nonionic detergent, $2C_{12}15G$, that contains a PEG moiety. Illum et al. (*FEBS Lett*., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett*., 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol*., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol*., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther*., 1992, 263, 25; Yamashita et al., *J. Pharm. Sci*., 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr*., 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel*., 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 199° C., 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol*., 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev*., 1995, 5, 115–121; Takakura et al., *Antisense & Nucl. Acid Drug Dev*., 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and NG-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-21—O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-21-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L) Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10%° C. The resulting crystalline product was collected by filtration, washed with ethyl ether (3×200 mL) and dried (40° C.., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert- Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and elated with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 Al 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$—, 2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy) ethyl)]-5-methyl uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using $MeOH:CH_2Cl_2:Et_3N$ (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P═O) oligonucleotides are synthesized on an automated DNA synthesizer (Applied Biosystems model 380B) using standard phosphoramidite chemistry with oxidation by iodine.

Phosphorothioates (P═S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P═O or P═S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)] Chimeric Phosphorothioate Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotides

[2'-O-(2-methoxyethyl phosphodiester]—[2'-deoxy phosphorothioate]—[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at. elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 6 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

HuVEC Cells:

The human umbilical vein endothilial cell line HuVEC was obtained from the American Type Culure Collection (Manassas, Va.). HuVEC cells were routinely cultured in EBM (Clonetics Corporation Walkersville, Md.) supplemented with SingleQuots supplements (Clonetics Corporation, Walkersville, Md.). Cells were routinely passaged by trypsinization and dilution when they reached 90% confluence were maintained for up to 15 passages. Cells were seeded into 96-well plates (Falcon-Primaria #3872) at a density of 10000 cells/well for use in RT-PCR analysis.

For Northern blotting or other analyses, cells may be seeded onto 100 mm or other standard tissue culture plates and treated similarly, using appropriate volumes of medium and oligonucleotide.

b.END Cells:

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Transforming Growth Factor-beta 3 Expression Antisense modulation of transforming growth factor-beta 3 expression can be assayed in a variety of ways known in the art. For example, transforming growth factor-beta 3 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of transforming growth factor-beta 3 can be quantitated in a variety of ways well known in the art, such as immunoprecipitation, Western blot analysis (immunoblotting), ELISA or fluorescence-activated cell sorting (FACS). Antibodies directed to transforming growth factor-beta 3 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology,* Volume 2, pp. 11.2.1–11.2.22, John Wiley & Sons, Inc., 1991.

Example 11

Poly(A)+mRNA Isolation

Poly(A)+mRNA was isolated according to Miura et al., *Clin. Chem.*, 1996, 42, 1758–1764. Other methods for poly(A)+mRNA isolation are taught in, for example, Ausubel, F. M. et al., *Current Protocols in Molecular Biology*, Volume 1, pp. 4.5.1–4.5.3, John Wiley & Sons, Inc., 1.993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 AL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Transforming Growth Factor-beta 3 mRNA Levels Quantitation of transforming growth factor-beta 3 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 $\mu$L PCR cocktail (1× TAQMAN™ buffer A, 5.5 mM $MgCl_2$, 300 $\mu$M each of dATP, dCTP and dGTP, 600 $\mu$M of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 $\mu$L total RNA solution. The RT reaction was carried out by incubation for 30 minutes at 480C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 $\mu$L of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human transforming growth factor-beta 3 were designed to hybridize to a human transforming growth factor-beta 3 sequence, using published sequence information (GenBank accession number NM_003239, incorporated herein as SEQ ID NO:3). For human transforming growth factor-beta 3 the PCR primers were: forward primer: ACCAATTACTGCTTCCGCAACT (SEQ ID NO: 4) reverse primer: GATCCTGTCGGAAGTCAATGTAGA (SEQ ID NO: 5) and the PCR probe was: FAM-AGGAGAACTGCTGTGTGCGCCCC-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: GAAGGTGAAGGTCGGAGTC (SEQ ID NO: 7) reverse primer: GAAGATGGTGATGGGATTTC (SEQ ID NO: 8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse transforming growth factor-beta 3 were designed to hybridize to a mouse transforming growth factor-beta 3 sequence, using published sequence information (GenBank accession number NM_009368, incorporated herein as SEQ ID NO:10). For mouse transforming growth factor-beta 3 the PCR primers were: forward primer: CAATTACTGCTTCCGCAACCT (SEQ ID NO:11) reverse primer: CTAGATCCTGCCGGAAGTCAA (SEQ ID NO: 12) and the PCR probe was: FAM-AGGAGAACTGCTGTGTACGCCCCCTTTAT-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were: forward primer: GGCAAATTCAACGGCACAGT (SEQ ID NO: 14) reverse primer: GGGTCTCGCTCCTGGAAGAT (SEQ ID NO: 15) and the PCR probe was: 5' JOE-AAGGCCGAGAATGGGAAGCTTGTCATC-TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Transforming Growth Factor-beta 3 mRNA levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, OH). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human transforming growth factor-beta 3, a human transforming growth factor-beta 3 specific probe was prepared by PCR using the forward primer ACCAATTACTGCTTCCGCAACT (SEQ ID NO: 4) and the reverse primer GATCCTGTCGGAAGTCAATGTAGA (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse transforming growth factor-beta 3, a mouse transforming growth factor-beta 3 specific probe was prepared by PCR using the forward primer CATTACTGCTTCCGCAACCT (SEQ ID NO:11) and the reverse primer CTAGATCCTGCCGGAAGTCAA (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Transforming Growth Factor-beta 3 Expression by Chimeric Phosphorothioate Oligonucleotides having 2'-MOE Wings and a Deoxy Gap In accordance with the present invention, a series of oligonucleotides were designed to target different regions of the human transforming growth factor-beta 3 RNA, using published sequences (GenBank accession number NM_003239, incorporated herein as SEQ ID NO: 3, and residues 138001–167000 of GenBank accession number AF107885, the complement of which is incorporated herein as SEQ ID NO: 17). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-methylcytidines. The compounds were analyzed for their effect on human transforming growth factor-beta 3 mRNA levels by quantitative real-time PCR as described in other examples herein. Data are averages from two experiments. If present, "N.D." indicates "no data".

TABLE 1

Inhibition of human transforming growth factor-beta 3 mRNA levels by chimeric phosphorothioate oligonucleotides having 2'-MOE wings and a deoxy gap

| ISIS# | REGION | TARGET SEQ ID NO | TARGET SITE | SEQUENCE | % INHIB | SEQ ID NO |
|---|---|---|---|---|---|---|
| 155638 | 5'UTR | 3 | 5 | ttgttgtccatgtgtctaaa | 69 | 18 |
| 155639 | 5'UTR | 3 | 76 | ttcaggacttccaggaagcg | 62 | 19 |
| 155640 | 5'UTR | 3 | 106 | aggtgcatgaactcactgca | 75 | 20 |
| 155641 | 5'UTR | 3 | 205 | cggcaaggcctggagaggaa | 0 | 21 |
| 155642 | Start Codon | 3 | 248 | aagtgcatcttcatgtgtga | 76 | 22 |
| 155643 | Start Codon | 3 | 253 | tttgcaagtgcatcttcatg | 87 | 23 |
| 155644 | Coding | 3 | 258 | agccctttgcaagtgcatct | 79 | 24 |
| 155645 | Coding | 3 | 263 | accagagccctttgcaagtg | 70 | 25 |
| 155646 | Coding | 3 | 284 | aagttcagcagggccaggac | 45 | 26 |
| 155647 | Coding | 3 | 313 | aagtggacagagagaggctg | 64 | 27 |
| 155648 | Coding | 3 | 316 | tgcaagtggacagagagagg | 47 | 28 |
| 155649 | Coding | 3 | 320 | gtggtgcaagtggacagaga | 85 | 29 |
| 155650 | Coding | 3 | 341 | ttgatgtggccgaagtccaa | 57 | 30 |
| 155651 | Coding | 3 | 346 | tcttcttgatgtggccgaag | 69 | 31 |
| 155652 | Coding | 3 | 351 | cctcttcttcttgatgtggc | 93 | 32 |
| 155653 | Coding | 3 | 356 | tccaccctcttcttcttgat | 70 | 33 |
| 155654 | coding | 3 | 361 | tggcttccaccctcttcttc | 72 | 34 |
| 155655 | Coding | 3 | 366 | cctaatggcttccaccctct | 87 | 35 |
| 155656 | Coding | 3 | 371 | tgtcccctaatggcttccac | 73 | 36 |
| 155657 | Coding | 3 | 376 | agatctgtcccctaatggct | 75 | 37 |
| 155658 | Coding | 3 | 380 | ctcaagatctgtcccctaat | 72 | 38 |
| 155659 | Coding | 3 | 383 | ttgctcaagatctgtcccct | 82 | 39 |
| 155660 | Coding | 3 | 430 | ggacgtgggtcatcaccgtt | 85 | 40 |
| 155661 | Coding | 3 | 566 | atcatgtcgaatttatggat | 43 | 41 |
| 155662 | Coding | 3 | 572 | ccctggatcatgtcgaattt | 70 | 42 |
| 155663 | coding | 3 | 653 | tccactgaggacacattgaa | 90 | 43 |
| 155664 | Coding | 3 | 656 | ttctccactgaggacacatt | 95 | 44 |
| 155665 | Coding | 3 | 660 | atttttctccactgaggaca | 90 | 45 |
| 155666 | Coding | 3 | 706 | tgggcacccgcaagacccgg | 90 | 46 |
| 155667 | Coding | 3 | 812 | gtgggcagattcttgccacc | 0 | 47 |
| 155668 | Coding | | 860 | cgcacagtgtcagtgacatc | 0 | 48 |
| 155669 | Coding | 3 | 929 | aaggtgtgacatggacagtg | 93 | 49 |
| 155670 | Coding | 3 | 934 | gctgaaaggtgtgacatgga | 84 | 50 |
| 155671 | Coding | 3 | 939 | attgggctgaaaggtgtgac | 0 | 51 |
| 155672 | Coding | 3 | 944 | tctccattgggctgaaaggt | 69 | 52 |
| 155673 | Coding | 3 | 983 | aatttgatttccatcacctc | 43 | 53 |
| 155674 | Coding | 3 | 1022 | tctccacggccatggtcatc | 57 | 54 |
| 155675 | Coding | 3 | 1163 | ttgcggaagcagtaattggt | 76 | 55 |
| 155676 | Coding | 3 | 1269 | tgagcagaagttggcatagt | 69 | 56 |
| 155677 | Coding | 3 | 1274 | gggcctgagcagaagttggc | 61 | 57 |
| 155678 | Coding | 3 | 1279 | ggcaagggcctgagcagaag | 50 | 58 |
| 155679 | Coding | 3 | 1295 | gcactgcggaggtatgggca | 50 | 59 |
| 155680 | Coding | 3 | 1346 | tcagggttcagagtgttgta | 50 | 60 |
| 155681 | Coding | 3 | 1457 | gacttcaccaccatgttgga | 37 | 61 |
| 155682 | Stop Codon | 3 | 1478 | gggtctcagctacatttaca | 54 | 62 |
| 155683 | 3'UTR | 3 | 1562 | agtgaggtttgttgcttgtg | 72 | 63 |
| 155684 | 3'UTR | 3 | 1619 | gaaacctccatctcagccat | 59 | 64 |
| 155685 | 3'UTR | 3 | 1703 | agagttcagccttcctctaa | 92 | 65 |
| 155686 | 3'UTR | 3 | 1807 | ttagggtagcccaaatccca | 66 | 66 |
| 155687 | 3'UTR | 3 | 1834 | agccattctctgcccttcct | 90 | 67 |
| 155688 | 3'UTR | 3 | 1870 | tcagatctgaagtgtcttcc | 94 | 68 |
| 155689 | 3'UTR | 3 | 1918 | tccagattccctagagcaga | 72 | 69 |
| 155690 | 3'UTR | 3 | 1929 | gtataacataatccagattc | 0 | 70 |
| 155691 | 3'UTR | 3 | 1943 | aaaatgcttgccttgtataa | 79 | 71 |
| 155692 | 3'UTR | 3 | 1979 | ctgggactttgtcttcgtaa | 95 | 72 |
| 155693 | 3'UTR | 3 | 2030 | ttgcaaaagtaatagatttg | 0 | 73 |
| 155694 | 3'UTR | 3 | 2051 | ttaattgatgtagaggacag | 0 | 74 |
| 155695 | 3'UTR | 3 | 2082 | ctggattttctccctgtagt | 86 | 75 |
| 155696 | 3'UTR | 3 | 2093 | aactgcatgacctggatttt | 7 | 76 |
| 155697 | 3'UTR | 3 | 2112 | atacagttgatgggccagga | 74 | 77 |
| 155698 | 3'UTR | 3 | 2126 | atccaaaaggcccaatacag | 36 | 78 |
| 155699 | 3'UTR | 3 | 2151 | ccaccctttcttctgcgttc | 87 | 79 |
| 155700 | 3'UTR | 3 | 2235 | gtctaaccaagtgtccaagg | 92 | 80 |
| 155701 | 3'UTR | 3 | 2280 | tgcatggaaccacaatccag | 96 | 81 |
| 155702 | 3'UTR | 3 | 2292 | atgccccaaggctgcatgga | 75 | 82 |

TABLE 1-continued

Inhibition of human transforming growth factor-beta 3 mRNA levels by chimeric phosphorothioate oligonucleotides having 2'-MOE wings and a deoxy gap

| ISIS# | REGION | TARGET SEQ ID NO | TARGET SITE | SEQUENCE | % INHIB | SEQ ID NO |
|---|---|---|---|---|---|---|
| 155703 | 3'UTR | 3 | 2335 | aatgaacacagggtcttgga | 87 | 83 |
| 155704 | 3'UTR | 3 | 2356 | cacctgcttccaggaacacc | 87 | 84 |
| 155705 | 3'UTR | 3 | 2361 | tgtagcacctgcttccagga | 28 | 85 |
| 155706 | 3'UTR | 3 | 2407 | agtcactgtgtggcacatgt | 4 | 86 |
| 155707 | 3'UTR | 3 | 2456 | agtaatattcatacttgtct | 23 | 87 |
| 155708 | 3'UTR | 3 | 2482 | atatttatttatacaaagat | 0 | 88 |
| 155709 | 3'UTR | 3 | 2534 | ctgttctagaaacaatattc | 62 | 89 |
| 155710 | Intron | 17 | 11878 | ctgctggaagcaaaggcagg | 0 | 90 |
| 155711 | Intron: Exon Junction | 17 | 12956 | gaggagttacctggaagagc | 0 | 91 |
| 155712 | In tron: Exon Junction | 17 | 13385 | gtccacctacctcttctcaa | 33 | 92 |
| 155713 | Intron | 17 | 18442 | atgccatctacatggttttt | 9 | 93 |
| 155714 | Intron: Exon Junction | 17 | 21023 | ttgtccacgcctgaagaagg | 56 | 94 |
| 155715 | Intron: Exon Junction | 17 | 21195 | ccagtctcaccggaagcagt | 1 | 95 |

As shown in Table 1, SEQ ID NOs 18, 19, 20, 22, 23, 24, 25, 26, 27, 28, 29, 30, 31, 32, 33, 34, 35, 36, 37, 38, 39, 40, 41, 42, 43, 44, 45, 46, 49, 50, 52, 53, 54, 55, 56, 57, 58, 59, 60, 62, 63, 64, 65, 66, 67, 68, 69, 71, 72, 75, 77, 79, 80, 81, 82, 83, 84, 89 and 94 demonstrated at least 40% inhibition of human transforming growth factor-beta 3 expression in this assay and are therefore preferred. The target sites to which these preferred sequences are complementary are herein referred to as "active sites" and are therefore preferred sites for targeting by compounds of the present invention.

Example 16

Antisense Inhibition of Mouse Transforming Growth Factor-beta 3 Expression by Chimeric Phosphorothioate Oligonucleotides having 2'-MOE Wings and a Deoxy Gap.

In accordance with the present invention, a second series of oligonucleotides were designed to target different regions of the mouse transforming growth factor-beta 3 RNA, using published sequences (GenBank accession number NM_009368, incorporated herein as SEQ ID NO: 10). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse transforming growth factor-beta 3 mRNA levels by quantitative real-time PCR as described in other examples herein. Data are averages from two experiments. If present, "N.D." indicates "no data".

TABLE 2

Inhibition of mouse transforming growth factor-beta 3 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 155654 | Coding | 10 | 712 | tggcttccaccctcttcttc | 61 | 34 |
| 155655 | Coding | 10 | 717 | cctaatggcttccaccctct | 68 | 35 |
| 155659 | Coding | 10 | 734 | ttgctcaagatctgtcccct | 36 | 39 |
| 155664 | Coding | 10 | 1007 | ttctccactgaggacacatt | 0 | 44 |
| 155666 | Coding | 10 | 1057 | tgggcacccgcaagacccgg | 80 | 46 |
| 185248 | 5'UTR | 10 | 17 | gctgggcggccgcaggccca | 31 | 96 |
| 185249 | 5'UTR | 10 | 48 | aatcaccagtgggtatgtgg | 23 | 97 |
| 185250 | 5'UTR | 10 | 190 | ctgcttggcgaggagaaagt | 22 | 98 |
| 185251 | 5'UTR | 10 | 209 | tatctgatatcgcccaacgc | 0 | 99 |
| 185252 | 5'UTR | 10 | 212 | ggatatctgatatcgcccaa | 25 | 100 |
| 185253 | 5'UTR | 10 | 324 | tctgactcccagcaggccag | 34 | 101 |
| 185254 | 5'UTR | 10 | 364 | taggatccttgtccatatgt | 0 | 102 |
| 185255 | 5'UTR | 10 | 407 | ccctggacgaagtagcggga | 12 | 103 |
| 185256 | 5'UTR | 10 | 416 | gctggcaacccctggacgaa | 54 | 104 |
| 185257 | 5'UTR | 10 | 449 | tgcgctgggtgagcttcagg | 53 | 105 |
| 185258 | 5'UTR | 10 | 537 | ggagaccccagtagaaaggg | 22 | 106 |
| 185259 | 5'UTR | 10 | 543 | caaggaggagaccccagtag | 7 | 107 |
| 185260 | Start Codon | 10 | 594 | catcttcatgtgtgagccca | 9 | 108 |
| 185261 | Coding | 10 | 625 | gggccaggactaccagagcc | 59 | 109 |
| 185262 | Coding | 10 | 648 | gctgattgtggccaagttca | 8 | 110 |
| 185263 | Coding | 10 | 657 | cagagagaggctgattgtgg | 38 | 111 |
| 185264 | Coding | 10 | 833 | atctcttccagcaactcccg | 0 | 112 |
| 185265 | Coding | 10 | 839 | ccgtgcatctcttccagcaa | 9 | 113 |
| 185266 | Coding | 10 | 878 | gactccgaggtctcctgagt | 68 | 114 |
| 185267 | Coding | 10 | 883 | actcagactccgaggtctcc | 37 | 115 |
| 185268 | Coding | 10 | 941 | tcattgtgctccgccagtcc | 29 | 116 |
| 185269 | Coding | 10 | 1238 | ttggactctctcctcaacag | 39 | 117 |
| 185270 | Coding | 10 | 1245 | acccaagttggactctctcc | 38 | 118 |
| 185271 | Coding | 10 | 1254 | gatttccagacccaagttgg | 31 | 119 |
| 185272 | Coding | 10 | 1303 | ccagtatgtctccattgggc | 77 | 120 |
| 185273 | Coding | 10 | 1320 | cacctcatgaacattttcca | 40 | 121 |
| 185274 | Coding | 10 | 1379 | cccaggtctccacggccatg | 59 | 122 |
| 185275 | Coding | 10 | 1399 | ccttttgcttcttgagacgc | 42 | 123 |
| 185276 | Coding | 10 | 1415 | tgtgggttgtggtgatcctt | 56 | 124 |
| 185277 | Coding | 10 | 1430 | atcatgaggatcaggtgtgg | 59 | 125 |
| 185278 | Coding | 10 | 1435 | ggatcatcatgaggatcagg | 10 | 126 |
| 185279 | Coding | 10 | 1459 | ctgggctgtccagtcggtgt | 57 | 127 |
| 185280 | Coding | 10 | 1484 | ctcttcttcctctgactgcc | 34 | 128 |
| 185281 | Coding | 10 | 1500 | attggtgtccagggccctct | 67 | 129 |
| 185282 | Coding | 10 | 1525 | tctcctccaggttgcggaag | 58 | 130 |
| 185283 | Coding | 10 | 1563 | ctgccggaagtcaatataaa | 18 | 131 |
| 185284 | Coding | 10 | 1580 | catttccagcctagatcctg | 30 | 132 |
| 185285 | Coding | 10 | 1667 | accgtgctatgggttgtgtc | 21 | 133 |
| 185286 | Coding | 10 | 1674 | tccaagcaccgtgctatggg | 30 | 134 |
| 185287 | Coding | 10 | 1721 | acgcagcatggcgaggcaga | 44 | 135 |
| 185288 | Stop Codon | 10 | 1832 | ggctggcctcagctgcactt | 77 | 136 |
| 185289 | 3'UTR | 10 | 1858 | gtggcagttttccctcctct | 3 | 137 |
| 185290 | 3'UTR | 10 | 1872 | agcagcagtctgtggtggca | 67 | 138 |
| 185291 | 3'UTR | 10 | 1900 | tgaggtctgtcgctttggtt | 0 | 139 |
| 185292 | 3'UTR | 10 | 1908 | ctctagggtgaggtctgtcg | 23 | 140 |
| 185293 | 3'UTR | 10 | 2015 | acactttctttaccacagtg | 0 | 141 |
| 185294 | 3'UTR | 10 | 2040 | cagtgtgccttcccctaacc | 25 | 142 |

TABLE 2-continued

Inhibition of mouse transforming growth factor-beta 3 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 185295 | 3'UTR | 10 | 2067 | tgcaccacagaaattccatg | 0 | 143 |
| 185296 | 3'UTR | 10 | 2073 | tctgcctgcaccacagaaat | 7 | 144 |
| 185297 | 3'UTR | 10 | 2108 | atgtccactcgctatccgtt | 42 | 145 |
| 185298 | 3'UTR | 10 | 2116 | cactcacaatgtccactcgc | 64 | 146 |
| 185299 | 3'UTR | 10 | 2142 | ttgtagggtagcccgaggcc | 33 | 147 |
| 185300 | 3'UTR | 10 | 2202 | cagacctgaaatgccttcca | 28 | 148 |
| 185301 | 3'UTR | 10 | 2216 | agcaaagctgacctcagacc | 1 | 149 |
| 185302 | 3'UTR | 10 | 2223 | tgcagtgagcaaagctgacc | 0 | 150 |
| 185303 | 3'UTR | 10 | 2238 | ctagagcagatgtactgcag | 0 | 151 |
| 185304 | 3'UTR | 10 | 2241 | tccctagagcagatgtactg | 0 | 152 |
| 185305 | 3'UTR | 10 | 2245 | caattccctagagcagatgt | 0 | 153 |
| 185306 | 3'UTR | 10 | 2254 | acgatatcccaattccctag | 2 | 154 |
| 185307 | 3'UTR | 10 | 2278 | aagaaaaatgcttggccgcc | 61 | 155 |
| 185308 | 3'UTR | 10 | 2292 | ggcttggtaaactgaagaaa | 26 | 156 |
| 185309 | 3'UTR | 10 | 2323 | ggcagtgcaagatatgattc | 38 | 157 |
| 185310 | 3'UTR | 10 | 2340 | gattgtccttaattccaggc | 46 | 158 |
| 185311 | 3'UTR | 10 | 2354 | ttgcagaaagaacggattgt | 0 | 159 |
| 185312 | 3'UTR | 10 | 2372 | atcgaggtgaaaagacagtt | 1 | 160 |
| 185313 | 3'UTR | 10 | 2390 | tgatgactcatgatgctgat | 3 | 161 |
| 185314 | 3'UTR | 10 | 2393 | ctgtgatgactcatgatgct | 25 | 162 |
| 185315 | 3'UTR | 10 | 2410 | gaaactaattacatgatctg | 4 | 163 |
| 185316 | 3'UTR | 10 | 2423 | agttgctggcccagaaacta | 65 | 164 |
| 185317 | 3'UTR | 10 | 2607 | ccccaggctatgtggactct | 43 | 165 |
| 185318 | 3'UTR | 10 | 2695 | tgggaggctccccggatact | 42 | 166 |
| 185319 | 3'UTR | 10 | 2781 | atttatacaaagattctgag | 0 | 167 |
| 185320 | 3'UTR | 10 | 2858 | accttaaagtgaggtcttta | 0 | 168 |

As shown in Table 2, SEQ ID NOs 34, 35, 46, 104, 105, 109, 114, 120, 121, 122, 123, 124, 125, 127, 129, 130, 135, 136, 138, 145, 146, 155, 158, 164, 165 and 166 demonstrated at least 40% inhibition of mouse transforming growth factor-beta 3 expression in this experiment and are therefore preferred. The target sites to which these preferred sequences are complementary are herein referred to as "active sites" and are therefore preferred sites for targeting by compounds of the present invention.

Example 17

Western Blot Analysis of Transforming Growth Factor-beta 3 Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to transforming growth factor-beta 3 is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 12 to 50 nucleobases in length targeted to nucleobases 653 through 679 of a coding region of a nucleic acid molecule of SEQ ID NO: 3 encoding human transforming growth factor-beta 3, wherein said compound wherein, the compound is an antisense oligonucleotide which specifically hybridizes with said regions and inhibits the expression of human transforming growth factor-beta 3.

2. The compound of claim 1 wherein the antisense oligonucleotide comprises at least one modified internucleoside linkage.

3. The compound of claim 2 wherein the modified internucleoside linkage is a phosphorothioate linkage.

4. The compound of claim 1 wherein the antisense oligonucleotide comprises at least one modified sugar moiety.

5. The compound of claim 1 wherein the modified sugar moiety is a 2'-O-methoxyethyl sugar moiety.

6. The compound of claim 1 wherein the antisense oligonucleotide comprises at least one modified nucleobase.

7. The compound of claim 6 wherein the modified nucleobase is a 5-methylcytosine.

8. The compound of claim 1 wherein the antisense oligonucleotide is a chimeric oligonucleotide.

9. A composition comprising the compound of claim 1 and pharmaceutically acceptable carrier or diluent.

10. The composition of claim 9 further comprising a colloidal dispersion system.

11. The composition of claim 9 wherein the compound is an antisense oligonucleotide.

12. A method of inhibiting the expression of transforming growth factor-beta 3 in cells or tissues comprising contacting said cells or tissues in vitro with the antisense compound of claim 1 so that expression transforming growth factor-beta 3 is inhibited.

* * * * *

UNITED STATES PATENT AND TRADEMARK OFFICE

CERTIFICATE OF CORRECTION

PATENT NO. : 6,884,787 B2
APPLICATION NO. : 09/906158
DATED : April 26, 2005
INVENTOR(S) : Susan M. Freier It is certified that error appears in the above-identified patent and that said Letters Patent is hereby corrected as shown below:

Title page,
Item [75], Inventors, delete "Brett P. Monia, Encinitas, CA (US);";

Column 133,
Line 25, delete ",";
Line 27, delete "regions" and insert -- region --;

Column 134,
Line 26, insert -- a -- between "and" and "pharmaceutically";
Line 35, insert -- of -- between "expression" and "transforming".

Signed and Sealed this

Twentieth Day of June, 2006

JON W. DUDAS
*Director of the United States Patent and Trademark Office*

SEQUENCE LISTING

```
<160> NUMBER OF SEQ ID NOS: 168

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1

tccgtcatcg ctcctcaggg                                    20


<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2

atgcattctg cccccaagga                                    20


<210> SEQ ID NO 3
<211> LENGTH: 2574
<212> TYPE: DNA
<213> ORGANISM: Homo sapiens
<220> FEATURE:
<221> NAME/KEY: CDS
```

-continued

```
<222> LOCATION: (254)...(1492)

<400> SEQUENCE: 3

cctgtttaga cacatggaca acaatcccag cgctacaagg cacacagtcc gcttcttcgt     60

cctcagggtt gccagcgctt cctggaagtc ctgaagctct cgcagtgcag tgagttcatg    120

caccttcttg ccaagcctca gtctttggga tctggggagg ccgcctggtt ttcctccctc    180

cttctgcacg tctgctgggg tctcttcctc tccaggcctt gccgtccccc tggcctctct    240

tcccagctca cac atg aag atg cac ttg caa agg gct ctg gtg gtc ctg       289
               Met Lys Met His Leu Gln Arg Ala Leu Val Val Leu
                 1               5                  10

gcc ctg ctg aac ttt gcc acg gtc agc ctc tct ctg tcc act tgc acc      337
Ala Leu Leu Asn Phe Ala Thr Val Ser Leu Ser Leu Ser Thr Cys Thr
         15                  20                  25

acc ttg gac ttc ggc cac atc aag aag aag agg gtg gaa gcc att agg      385
Thr Leu Asp Phe Gly His Ile Lys Lys Lys Arg Val Glu Ala Ile Arg
     30                  35                  40

gga cag atc ttg agc aag ctc agg ctc acc agc ccc cct gag cca acg      433
Gly Gln Ile Leu Ser Lys Leu Arg Leu Thr Ser Pro Pro Glu Pro Thr
 45                  50                  55                  60

gtg atg acc cac gtc ccc tat cag gtc ctg gcc ctt tac aac agc acc      481
Val Met Thr His Val Pro Tyr Gln Val Leu Ala Leu Tyr Asn Ser Thr
                 65                  70                  75

cgg gag ctg ctg gag gag atg cat ggg gag agg gag gaa ggc tgc acc      529
Arg Glu Leu Leu Glu Glu Met His Gly Glu Arg Glu Glu Gly Cys Thr
             80                  85                  90

cag gaa aac acc gag tcg gaa tac tat gcc aaa gaa atc cat aaa ttc      577
Gln Glu Asn Thr Glu Ser Glu Tyr Tyr Ala Lys Glu Ile His Lys Phe
         95                 100                 105

gac atg atc cag ggg ctg gcg gag cac aac gaa ctg gct gtc tgc cct      625
Asp Met Ile Gln Gly Leu Ala Glu His Asn Glu Leu Ala Val Cys Pro
    110                 115                 120

aaa gga att acc tcc aag gtt ttc cgc ttc aat gtg tcc tca gtg gag      673
Lys Gly Ile Thr Ser Lys Val Phe Arg Phe Asn Val Ser Ser Val Glu
125                 130                 135                 140

aaa aat aga acc aac cta ttc cga gca gaa ttc cgg gtc ttg cgg gtg      721
Lys Asn Arg Thr Asn Leu Phe Arg Ala Glu Phe Arg Val Leu Arg Val
                145                 150                 155

ccc aac ccc agc tct aag cgg aat gag cag agg atc gag ctc ttc cag      769
Pro Asn Pro Ser Ser Lys Arg Asn Glu Gln Arg Ile Glu Leu Phe Gln
            160                 165                 170

atc ctt cgg cca gat gag cac att gcc aaa cag cgc tat atc ggt ggc      817
Ile Leu Arg Pro Asp Glu His Ile Ala Lys Gln Arg Tyr Ile Gly Gly
        175                 180                 185

aag aat ctg ccc aca cgg ggc act gcc gag tgg ctg tcc ttt gat gtc      865
Lys Asn Leu Pro Thr Arg Gly Thr Ala Glu Trp Leu Ser Phe Asp Val
    190                 195                 200

act gac act gtg cgt gag tgg ctg ttg aga aga gag tcc aac tta ggt      913
Thr Asp Thr Val Arg Glu Trp Leu Leu Arg Arg Glu Ser Asn Leu Gly
205                 210                 215                 220

cta gaa atc agc att cac tgt cca tgt cac acc ttt cag ccc aat gga      961
Leu Glu Ile Ser Ile His Cys Pro Cys His Thr Phe Gln Pro Asn Gly
                225                 230                 235

gat atc ctg gaa aac att cac gag gtg atg gaa atc aaa ttc aaa ggc     1009
Asp Ile Leu Glu Asn Ile His Glu Val Met Glu Ile Lys Phe Lys Gly
            240                 245                 250

gtg gac aat gag gat gac cat ggc cgt gga gat ctg ggg cgc ctc aag     1057
Val Asp Asn Glu Asp Asp His Gly Arg Gly Asp Leu Gly Arg Leu Lys
        255                 260                 265
```

-continued

```
aag cag aag gat cac cac aac cct cat cta atc ctc atg atg att ccc     1105
Lys Gln Lys Asp His His Asn Pro His Leu Ile Leu Met Met Ile Pro
    270                 275                 280

cca cac cgg ctc gac aac ccg ggc cag ggg ggt cag agg aag aag cgg     1153
Pro His Arg Leu Asp Asn Pro Gly Gln Gly Gly Gln Arg Lys Lys Arg
285                 290                 295                 300

gct ttg gac acc aat tac tgc ttc cgc aac ttg gag gag aac tgc tgt     1201
Ala Leu Asp Thr Asn Tyr Cys Phe Arg Asn Leu Glu Glu Asn Cys Cys
                305                 310                 315

gtg cgc ccc ctc tac att gac ttc cga cag gat ctg ggc tgg aag tgg     1249
Val Arg Pro Leu Tyr Ile Asp Phe Arg Gln Asp Leu Gly Trp Lys Trp
            320                 325                 330

gtc cat gaa cct aag ggc tac tat gcc aac ttc tgc tca ggc cct tgc     1297
Val His Glu Pro Lys Gly Tyr Tyr Ala Asn Phe Cys Ser Gly Pro Cys
        335                 340                 345

cca tac ctc cgc agt gca gac aca acc cac agc acg gtg ctg gga ctg     1345
Pro Tyr Leu Arg Ser Ala Asp Thr Thr His Ser Thr Val Leu Gly Leu
    350                 355                 360

tac aac act ctg aac cct gaa gca tct gcc tcg cct tgc tgc gtg ccc     1393
Tyr Asn Thr Leu Asn Pro Glu Ala Ser Ala Ser Pro Cys Cys Val Pro
365                 370                 375                 380

cag gac ctg gag ccc ctg acc atc ctg tac tat gtt ggg agg acc ccc     1441
Gln Asp Leu Glu Pro Leu Thr Ile Leu Tyr Tyr Val Gly Arg Thr Pro
                385                 390                 395

aaa gtg gag cag ctc tcc aac atg gtg gtg aag tct tgt aaa tgt agc     1489
Lys Val Glu Gln Leu Ser Asn Met Val Val Lys Ser Cys Lys Cys Ser
            400                 405                 410

tga gaccccacgt gcgacagaga gaggggagag agaaccacca ctgcctgact         1542

gcccgctcct cgggaaacac acaagcaaca aacctcactg agaggcctgg agcccacaac   1602

cttcggctcc gggcaaatgg ctgagatgga ggtttccttt tggaacattt ctttcttgct   1662

ggctctgaga atcacggtgg taaagaaagt gtgggtttgg ttagaggaag gctgaactct   1722

tcagaacaca cagactttct gtgacgcaga cagaggggat ggggatagag gaaagggatg   1782

gtaagttgag atgttgtgtg gcaatgggat ttgggctacc ctaaagggag aaggaagggc   1842

agagaatggc tgggtcaggg ccagactgga agacacttca gatctgaggt tggatttgct   1902

cattgctgta ccacatctgc tctagggaat ctggattatg ttatacaagg caagcatttt   1962

tttttttaaa gacaggttac gaagacaaag tcccagaatt gtatctcata ctgtctggga   2022

ttaagggcaa atctattact tttgcaaact gtcctctaca tcaattaaca tcgtgggtca   2082

ctacagggag aaaatccagg tcatgcagtt cctggcccat caactgtatt gggccttttg   2142

gatatgctga acgcagaaga aagggtggaa atcaaccctc tcctgtctgc cctctgggtc   2202

cctcctctca cctctccctc gatcatattt ccccttggac acttggttag acgccttcca   2262

ggtcaggatg cacatttctg gattgtggtt ccatgcagcc ttggggcatt atgggtcttc   2322

ccccacttcc cctccaagac cctgtgttca tttggtgttc ctggaagcag gtgctacaac   2382

atgtgaggca ttcggggaag ctgcacatgt gccacacagt gacttggccc cagacgcata   2442

gactgaggta taaagacaag tatgaatatt actctcaaaa tctttgtata aataaatatt   2502

tttggggcat cctggatgat ttcatcttct ggaatattgt ttctagaaca gtaaaagcct   2562

tattctaagg tg                                                       2574
```

<210> SEQ ID NO 4
<211> LENGTH: 22
<212> TYPE: DNA

-continued

<213> ORGANISM: Artificial Sequence
<220> FEATURE:
<223> OTHER INFORMATION: PCR Primer

<400> SEQUENCE: 4
accaattact gcttccgcaa ct 22

<210> SEQ ID NO 5
<211> LENGTH: 24
<212> TYPE: DNA
<213> ORGANISM: Artificial Sequence
<220> FEATURE:
<223> OTHER INFORMATION: PCR Primer

<400> SEQUENCE: 5
gatcctgtcg gaagtcaatg taga 24

<210> SEQ ID NO 6
<211> LENGTH: 23
<212> TYPE: DNA
<213> ORGANISM: Artificial Sequence
<220> FEATURE:
<223> OTHER INFORMATION: PCR Probe

<400> SEQUENCE: 6
aggagaactg ctgtgtgcgc ccc 23

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc 19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc 20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc 20

<210> SEQ ID NO 10
<211> LENGTH: 2879
<212> TYPE: DNA
<213> ORGANISM: Mus musculus
<220> FEATURE:
<221> NAME/KEY: CDS
<222> LOCATION: (611)...(1843)

<400> SEQUENCE: 10

-continued

```
ccgccccacc tttagctggg cctgcggccg cccagccctg cctctcccca catacccact     60

ggtgattttt ttttttgaa aaaacattcc ttttttttctt cgcttttctt attttccctt    120

cagggcaagg caaagagctt gattttttgg gacccagcca tcctcttctg cactttcttt    180

aaaatactca ctttctcctc gccaagcagc gttgggcgat atcagatatc cgctctattt    240

atttttacct aaggaaaaac tccagctctc ttcccactcc cagctgcctt gccacccctc    300

ccaaccctcg gcttgccctc cacctggcct gctgggagtc agagcccggc agaacctgtt    360

tagacatatg gacaaggatc ctagctctac ccagcacacg gtccggtccc gctacttcgt    420

ccaggggttg ccagcgcttc ctgggagtcc tgaagctcac ccagcgcagt gagttcatgc    480

accctcttgc caagcctcag gctttgggat ctggggagga cgcctggttt tcctcccccct    540

ttctactggg gtctcctcct tgccaggcct ccccagtccc ctggcctcgt tcctgggctc    600

acacatgaag  atg cac ttg caa agg gct ctg gta gtc ctg gcc ctg ctg      649
            Met His Leu Gln Arg Ala Leu Val Val Leu Ala Leu Leu
             1               5                  10

aac ttg gcc aca atc agc ctc tct ctg tcc act tgc acc acg ttg gac      697
Asn Leu Ala Thr Ile Ser Leu Ser Leu Ser Thr Cys Thr Thr Leu Asp
     15                  20                  25

ttc ggc cac atc aag aag aag agg gtg gaa gcc att agg gga cag atc      745
Phe Gly His Ile Lys Lys Lys Arg Val Glu Ala Ile Arg Gly Gln Ile
 30                  35                  40                  45

ttg agc aag ctc agg ctc acc agc ccc cct gag cca tcg gtg atg acc      793
Leu Ser Lys Leu Arg Leu Thr Ser Pro Pro Glu Pro Ser Val Met Thr
                 50                  55                  60

cac gtc ccc tat cag gtc ctg gca ctt tac aac agc acc cgg gag ttg      841
His Val Pro Tyr Gln Val Leu Ala Leu Tyr Asn Ser Thr Arg Glu Leu
             65                  70                  75

ctg gaa gag atg cac ggg gag agg gag gaa ggc tgc act cag gag acc      889
Leu Glu Glu Met His Gly Glu Arg Glu Glu Gly Cys Thr Gln Glu Thr
         80                  85                  90

tcg gag tct gag tac tat gcc aaa gag atc cat aaa ttc gac atg atc      937
Ser Glu Ser Glu Tyr Tyr Ala Lys Glu Ile His Lys Phe Asp Met Ile
     95                 100                 105

cag gga ctg gcg gag cac aat gaa ctg gcc gtc tgc ccc aaa gga att      985
Gln Gly Leu Ala Glu His Asn Glu Leu Ala Val Cys Pro Lys Gly Ile
110                 115                 120                 125

acc tct aag gtt ttt cgt ttc aat gtg tcc tca gtg gag aaa aat gga     1033
Thr Ser Lys Val Phe Arg Phe Asn Val Ser Ser Val Glu Lys Asn Gly
                130                 135                 140

acc aat ctg ttc cgg gca gag ttc cgg gtc ttg cgg gtg ccc aac ccc     1081
Thr Asn Leu Phe Arg Ala Glu Phe Arg Val Leu Arg Val Pro Asn Pro
            145                 150                 155

agc tcc aag cgc aca gag cag aga att gag ctc ttc cag ata ctt cga     1129
Ser Ser Lys Arg Thr Glu Gln Arg Ile Glu Leu Phe Gln Ile Leu Arg
        160                 165                 170

ccg gat gag cac ata gcc aag cag cgc tac ata ggt ggc aag aat ctg     1177
Pro Asp Glu His Ile Ala Lys Gln Arg Tyr Ile Gly Gly Lys Asn Leu
    175                 180                 185

ccc aca agg ggc acc gct gaa tgg ctg tct ttc gat gtc act gac act     1225
Pro Thr Arg Gly Thr Ala Glu Trp Leu Ser Phe Asp Val Thr Asp Thr
190                 195                 200                 205

gtg cgc gag tgg ctg ttg agg aga gag tcc aac ttg ggt ctg gaa atc     1273
Val Arg Glu Trp Leu Leu Arg Arg Glu Ser Asn Leu Gly Leu Glu Ile
                210                 215                 220

agc atc cac tgt cca tgt cac acc ttt cag ccc aat gga gac ata ctg     1321
Ser Ile His Cys Pro Cys His Thr Phe Gln Pro Asn Gly Asp Ile Leu
            225                 230                 235
```

-continued

```
gaa aat gtt cat gag gtg atg gaa atc aaa ttc aaa gga gtg gac aat     1369
Glu Asn Val His Glu Val Met Glu Ile Lys Phe Lys Gly Val Asp Asn
        240                 245                 250

gaa gat gac cat ggc cgt gga gac ctg ggg cgt ctc aag aag caa aag     1417
Glu Asp Asp His Gly Arg Gly Asp Leu Gly Arg Leu Lys Lys Gln Lys
    255                 260                 265

gat cac cac aac cca cac ctg atc ctc atg atg atc ccc cca cac cga     1465
Asp His His Asn Pro His Leu Ile Leu Met Met Ile Pro Pro His Arg
270                 275                 280                 285

ctg gac agc cca ggc cag ggc agt cag agg aag aag agg gcc ctg gac     1513
Leu Asp Ser Pro Gly Gln Gly Ser Gln Arg Lys Lys Arg Ala Leu Asp
                290                 295                 300

acc aat tac tgc ttc cgc aac ctg gag gag aac tgc tgt gta cgc ccc     1561
Thr Asn Tyr Cys Phe Arg Asn Leu Glu Glu Asn Cys Cys Val Arg Pro
            305                 310                 315

ctt tat att gac ttc cgg cag gat cta ggc tgg aaa tgg gtc cac gaa     1609
Leu Tyr Ile Asp Phe Arg Gln Asp Leu Gly Trp Lys Trp Val His Glu
        320                 325                 330

cct aag ggt tac tat gcc aac ttc tgc tca ggc cct tgc cca tac ctc     1657
Pro Lys Gly Tyr Tyr Ala Asn Phe Cys Ser Gly Pro Cys Pro Tyr Leu
    335                 340                 345

cgc agc gca gac aca acc cat agc acg gtg ctt gga cta tac aac acc     1705
Arg Ser Ala Asp Thr Thr His Ser Thr Val Leu Gly Leu Tyr Asn Thr
350                 355                 360                 365

ctg aac cca gag gcg tct gcc tcg cca tgc tgc gtc ccc cag gac ctg     1753
Leu Asn Pro Glu Ala Ser Ala Ser Pro Cys Cys Val Pro Gln Asp Leu
                370                 375                 380

gag ccc ctg acc atc ttg tac tat gtg ggc aga acc ccc aag gtg gag     1801
Glu Pro Leu Thr Ile Leu Tyr Tyr Val Gly Arg Thr Pro Lys Val Glu
            385                 390                 395

cag ctg tcc aac atg gtg gtg aag tcg tgt aag tgc agc tga ggccagcctg  1853
Gln Leu Ser Asn Met Val Val Lys Ser Cys Lys Cys Ser
        400                 405                 410

ccacagagga gggaaaactg ccaccacaga ctgctgctcc ttggaaaacc aaagcgacag   1913

acctcaccct agaggcctgg agcccagaag ccctggctcc cggcgaaagg ccgagaggga   1973

ggcttccttc tggaacattt ctttctgcta gctttgagaa tcactgtggt aaagaaagtg   2033

tgggttggtt aggggaaggc acactgttga gaacatggaa tttctgtggt gcaggcagag   2093

gtggtggggt agagaacgga tagcgagtgg acattgtgag tggcaatggg cctcgggcta   2153

ccctacaaaa gatgaagggt agagtggtca gtcaggtgaa ggccagactg gaaggcattt   2213

caggtctgag gtcagctttg ctcactgcag tacatctgct ctagggaatt gggatatcgt   2273

tagaggcggc caagcatttt tcttcagttt accaagccaa agtcccctgg aatcatatct   2333

tgcactgcct ggaattaagg acaatccgtt ctttctgcaa ctgtcttttc acctcgatca   2393

gcatcatgag tcatcacaga tcatgtaatt agtttctggg ccagcaacta gctatctcag   2453

gtcccttaga gatgctggac tcaaaagcag aggtcagaat tggttctctc atgtattccc   2513

tgggggcccc tcctcctgcc ttccttcttg gccgcatttc cccttggata tttggctaga   2573

caccttccgg gtcagggtgt attctccgga ttcagagtcc acatagcctg ggcgccatt    2633

tccctcctac cctagacccc gttgctcccc aggtgttcct ggaagcaggt gctacatgcc   2693

aagtatccgg ggagcctccc atgtctgaca tgatgactcg gccccagatg cacagactga   2753

agtataaaga caaatacaaa tattactctc agaatctttg tataaataaa tatttttggg   2813

gaatcatgga tgacttcatc tcctggaagg ttcttctaaa acagtaaaga cctcacttta   2873
```

|                                                                 | -continued |
|---|---|
| aggtgt | 2879 |

```
<210> SEQ ID NO 11
<211> LENGTH: 21
<212> TYPE: DNA
<213> ORGANISM: Artificial Sequence
<220> FEATURE:
<223> OTHER INFORMATION: PCR Primer

<400> SEQUENCE: 11

caattactgc ttccgcaacc t                                              21

<210> SEQ ID NO 12
<211> LENGTH: 21
<212> TYPE: DNA
<213> ORGANISM: Artificial Sequence
<220> FEATURE:
<223> OTHER INFORMATION: PCR Primer

<400> SEQUENCE: 12

ctagatcctg ccggaagtca a                                              21

<210> SEQ ID NO 13
<211> LENGTH: 29
<212> TYPE: DNA
<213> ORGANISM: Artificial Sequence
<220> FEATURE:
<223> OTHER INFORMATION: PCR Probe

<400> SEQUENCE: 13

aggagaactg ctgtgtacgc cccctttat                                      29

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14

ggcaaattca acggcacagt                                                20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15

gggtctcgct cctggaagat                                                20

<210> SEQ ID NO 16
<211> LENGTH: 27
<212> TYPE: DNA
<213> ORGANISM: Artificial Sequence
<220> FEATURE:
<223> OTHER INFORMATION: PCR Probe

<400> SEQUENCE: 16

aaggccgaga atgggaagct tgtcatc                                        27

<210> SEQ ID NO 17
<211> LENGTH: 29000
<212> TYPE: DNA
<213> ORGANISM: Homo sapiens
```

-continued

<220> FEATURE:

<400> SEQUENCE: 17

```
ttatctctaa gatcctttgt taacttgctt ctcagtgaga atactttgtt agattttaat     60
ctgaagaaac actcattgcc aaaaatccaa gacagatgaa atataggctc caatgaatcc    120
cttgttccct tcttcttcgg caccagatga ggaagaaggg attaatcttt ggatttttcc    180
atttcttgta agctcacagc atacgaccat caccttatag tcagtttcca gaccttcacc    240
cccacttctt ccccaacttg ctgaaaacag aaggcaaatg gtcctcactc tgggcagaga    300
ggtaccctgc agtagtagct tccagaactt gcttagcacc tgaatcacgt gtgaggtttg    360
taaagaaaca gagatgccag ggcctcagct ctggagactg atttggtaga ggtggagtcc    420
aaaaaagtat aactttaata attttccttc ctatcttgca actgtctgct caaaggcctt    480
cccttatcac cctatttgaa actgcaacat cccccaacct aggcacaccc catcctcctt    540
ccctgcttga ttttctgcca caccacattt gtttgtttgc ttgtctgttt gagacacggt    600
cttgctctgt cgtccaggct ggagtgcagt ggtgcaatct tggccccctg taaactctgc    660
ctccctggct caagtgatta tcctgcctca gcctcccaag tagatgcctg cgccaacatg    720
ccgggctaat ttttccattt ttttgtagag actgggtttc gccgtgttgc tggggctggt    780
ctcgaattcc tgagctcaag taatcctcct gcatgggcct ccccaaatgc tgggattaca    840
ggcgtgagcc actgcacctg gctcagcact ttttaccgta ctacatcatt tacatattta    900
tttagtttat cgcctcctcc actgccccac ccctgcctct aaaataaaat ttccctgagg    960
gcaggagttt tgtttcgttc actgatattc ttcacagagc ctagaatagt gcctggtata   1020
tagtaaacat taaacttttt ctgaaatttc agaggcagta tagcatagta attaagtcca   1080
gaatctggca acgtcctggg tccaaatccc aacagctgac acctaataac tatgtgacct   1140
tgggcaagtt acttttaaag tttctacccc taggtttccc attggttttg caaatgaaag   1200
taatgcctac ccaagctaga tagcctgtgt aaaatatcgc ctccatcact cacaagcagt   1260
gtggtctgta aaaaaaaaaa caaaaaactc tatgcctcag tttcctcatc cgtaaagtga   1320
cccaccgctg tgctgggata cagagaacag ccccttcagt tagtggcctg gaagccagac   1380
ctctcagaaa gggtccagga aggctggagt gagatggggt gggagcggca ctcactctca   1440
ggaaagttca gttcagaggc aagccctgtg ttgcggggtg cggggagcca cgtgccctac   1500
cctcccttgg ctgctcgtgg gaaaaggcct agaggttcgg gccgagaaga ggagcgaaag   1560
cacagagccg acttcccctc acccatctgg gaaatgggct cgggccaact gctgacttcg   1620
cgctcgctgg cgcagctccc tgcggagacc tcggcgggga gggaggctga acatctggat   1680
gacatttctg cgagagcggc tccggagcgg cggtcgggga gggagaggtg cgctcgtgcg   1740
cacgtcgggc cgggagggag gcgattcctc ggggcctggg tcttgttttt ctcgctctct   1800
accgcagccc cttctcccgc ccctcagccc ccaccccgca gcccccagcc cccgagcctc   1860
cccggctccc gaccagccga gctccttcac tggcggcctc gcctcgccag agggcaccct   1920
cgatcttccg gaaaacgcca ccatttttca ctgcccctgg agcgtctcca ggcttctgcc   1980
cgcctcccga ctccgatctt gtcaatgaag aatcgggcca ggatcgccgc ggagcggacg   2040
ccgaccctcc gacccggctc gcaggctggg agtcccctct gcgaggctgg catggccgcc   2100
cctaccgggt cccgcgccct ctgcggaccc tgccccgggt tgggcctggc ccgcgggcgg   2160
ccccgggacc gggggaccag gagggagagt agacgcgggc cgcggacggc gcggactgac   2220
agctggcgag agggcgccgg ggctggggga aagggaggga gggggctcat cggagtaact   2280
```

-continued

```
ttccagaaaa acagccaacg tgtggcagga gtgattccaa gaggggaaaa aaagttcagc   2340
taccacgtcg aacgagagga ctcgcaaagt atttttcaaa agggctcggc ttttcctgtg   2400
cctgtttaaa acattaacat cgtgcagcaa aagaggctgc gtgcgctggt ccctccctcc   2460
cccaccccag gccagagacg tcatgggagg gaggtataaa atttcagcag agagaaatag   2520
agaaagcagt gtgtgtgcat gtgtgtgtgt gtgagagaga gagggagagg agcgagaggg   2580
agagggagag ggagagagag aaagggaggg aagcagagag tcaagtccaa gggaatgagc   2640
gagagaggca gagacagggg aagaggcgtg cgagagaagg aataacagct ttccggagca   2700
ggcgtgccgt gaactggctt ctattttatt ttattttttt ctccttttta ttttttaaag   2760
agaagcaggg gacagaagca atggccgagg cagaagacaa gccgaggtgc tggtgaccct   2820
gggcgtctga gtggatgatt ggggctgctg cgctcagagg cctgcctccc tgccttccaa   2880
tgcatataac cccacacccc agccaatgaa gacgagaggc agcgtgaaca aagtcattta   2940
gaaagccccc gaggaagtgt aaacaaaaga gaaagcatga atggagtgcc tgagagacaa   3000
gtgtgtcctg tactgccccc acctttagct gggccagcaa ctgcccggcc ctgcttctcc   3060
ccacctactc actggtgatc tttttttttt tacttttttt tccctttttct tttccattct   3120
cttttcttat tttctttcaa ggcaaggcaa ggattttgat tttgggaccc agccatggtc   3180
cttctgcttc ttctttaaaa tacccacttt ctccccatcg ccaagcggcg tttggcaata   3240
tcagatatcc actctattta tttttaccta aggaaaaact ccagctccct tcccactccc   3300
agctgccttg ccacccctcc cagccctctg cttgccctcc acctggcctg ctgggagtca   3360
gagcccagca aaacctgttt agacacatgg acaagaatcc cagcgctaca aggcacacag   3420
tccgcttctt cgtcctcagg gttgccagcg cttcctggaa gtcctgaagc tctcgcagtg   3480
cagtgagttc atgcaccttc ttgccaagcc tcagtctttg ggatctgggg aggccgcctg   3540
gttttcctcc ctccttctgc acgtctgctg ggtctcttc ctctccaggc cttgccgtcc   3600
ccctggcctc tcttcccagc tcacacatga agatgcactt gcaaagggct ctggtggtcc   3660
tggccctgct gaactttgcc acggtcagcc tctctctgtc cacttgcacc accttggact   3720
tcggccacat caagaagaag agggtggaag ccattagggg acagatcttg agcaagctca   3780
ggctcaccag ccccccctgag ccaacggtga tgacccacgt cccctatcag gtcctggccc   3840
tttacaacag cacccgggag ctgctggagg agatgcatgg ggagagggag gaaggctgca   3900
cccaggaaaa caccgagtcg gaatactatg ccaaagaaat ccataaattc gacatgatcc   3960
aggggctggc ggagcacagt aagtccaaat tctcgctggg gtgtctgctc tggagggtct   4020
gaactggagc tgggagctct gcagaggggg gcctagtgct ggccacacag cagggtgccc   4080
caggattcac cagcaccaag gctcaggatg tgcgatgctc ctccgttggg gctggggagg   4140
tgggtgggga aggagataga gccattctgt taagagccgg cgcttctggg aggccaggag   4200
ccctggagct gagtggcttg ctgaattcac atcacatcct tgactgattt taatttggaa   4260
ttacattgtg ctgtccaggg aaacatatgt attcttgcac atgcgatcgt atcagtaact   4320
gtaagcatct gggtgccata aaggggaagg ccggctctgt caggagccct tacggttctc   4380
agtgtggaga cctcatcttc tccctgcttt tcacaactca ttgtgacacg tctccgtttc   4440
agtttttcca gttcttggga agaagaatac ctgccccaaa ttaatgtctg tcaagctttt   4500
tgaagcccag gcaggagaca gcttcttgct gcctgggccc tttggtctac cccacccacg   4560
tgacccacga gacccacgtg agctgtgtgt gtggaaggaa gagggtatgc acgaatgttc   4620
```

-continued

```
ccagggccgt gtactttagg gtgacatgca gtcttgtgca gtagacagat tcatgtgctc   4680
aaaatgggcg ccctccaggc cggtgggcac ggggagagcg ggttttggct gtggatgcgt   4740
agaggaggct ggcgcccttt gtgtctgcgt gtcacgggag agcgggtgga ggggtggcag   4800
tgggtgcatg gtgggggggg gggatatgtc tgggagcctg ccgtcccagg aggctctgtc   4860
tgcatggagg agccgggcgg cttctgggcg agatgtctgt gtgtgttggt acacgtgtgg   4920
aagtcatatg tgtttactga aggggatttt aaaaacctca atacaagaga gagaaatttg   4980
gcagatgttg agaaactgac agcccaggaa agaggaatgt gagccactcg tgggccgtag   5040
actccgggag cagctctgtt tgcttttcct accagcaggt gtcctcgccg ccctgactac   5100
ctcagcccag gcccacctgg gaggtgggca gctcctggag tggggtggag ggcatgggat   5160
ggagctggca ggcaggggag ggtggtcagc agagcacaca gcaaggggtg aaaggaacct   5220
ggctggagag aaggaacagg agtgggtacc gatgggtgga ccagctctgg ctggaggtgc   5280
aaaggccccg ttcacggctc cacgccaggc agaggagcct gtggttactg gcgaggggtt   5340
cccgctccag cttcctgtgg ctgcctggag cgcctttctt caggatgtgg ctgccatgtg   5400
gggcggaggc tggaggccga tgcagagcta ctactccctg cccagggtct ctgggtgggg   5460
ctggctcaga gacccacagt tcccagaggc acctagcagc tcgatggcca aggctccaac   5520
tccctgggaa cccaccaacg cgggagatag tgaccacaag catcagagga aggtcgaaat   5580
ctgaggccgg caggagaggt gtgaggagag tccagggcaa gagggcagga ctcagacctt   5640
catggtctgg gtcagcagga ggagtccaag ggaggaagca ttctgagtca ccaggacccc   5700
cccatcccgg aatcctgagc tgagaatgaa tgagccacgt ggaggcaagg ccatgcaggt   5760
gcaagtggac actgattttg tgcagactca aagcacaaat agcagatgtc cttgggaaaa   5820
gcccgggcag ggccccatag atgctgggca gcttccaggc tgcagtacca agaccttaca   5880
actgcaacag atgggtggat gtggggttat ggagcaatgg tctggcctgg ggcaacccag   5940
cacagtgagc aggatgctgt tcaggatgct ggggaggagc caacgtgcga tgctatgagg   6000
ctcacaggta caaaccggaa gcaggcagac tctgcagctg ttggaggtga cttggaggct   6060
gagcagacgg acctgggccc gccctgcagc tggtcgggtg ctgagcccac cccagagagg   6120
cagacacaca aggcacacta actataaaga aggcagtggg caggtgctga gcaggagcag   6180
agagccatca tcaggggctt gcaaggcggc ggggcggggt gggggaagga agcctgtctt   6240
taactcatga gggcagacag gggtgacacc aggtctgtgg tggggcacag caggtctcca   6300
atgccagagc ctctgctggg aggtcatgag atcacgttct gttccatatt tcctcacttc   6360
tggccacttc cctgacccag tgaacatgca ttcaaaggaa agtgacagta ggagccaggg   6420
caaggagata gaggtccctg gagaggaaaa tgaaagagga aatacttttt agtagtgcag   6480
gagaaagggc accaaggtga gagcagagag gaaggccttt tcctaaataa ccttttctcc   6540
ctgttttaca gataaggaaa ctgagacctg gattgcttaa gtaatttgtc caaaaagagc   6600
agggacccta acctagacat tctgtgtgca ggacgcatgt agttaagcac tcatttatat   6660
gtaaaataca cgttgtaagt gttaccttta acctccttta acctttaggg ttcagtagaa   6720
ctttgattta taacataaat gaatcatgtg ttggaccaag caggagaggt cagagttatt   6780
atcttagtaa cccaggtggc agattgcaca atgataactg gatttgttct tccttagctc   6840
tgcatttttt tttttttttt tttgcccggg agattcatac tgccacaaat gttctcccta   6900
atttaatgaa ggagttttct ttatttaatg aagagtctca agcaggttaa gcaaccgcag   6960
ctacgtaaaa gtgacctctc tgagcctcag tttccccagc tgtaaagtta gagatgattt   7020
```

-continued

```
ccaaactcct tttcagctga aagaatttta taattccatc tgggatgaat cagcagagcc   7080
tctattgggg agtatgggca agactctgta atccttttc taattctcca ggattttact   7140
gtcgggaggg agtagagagt ttctctgacc ccatgtgatg ggaaaggaca cagctttttt   7200
acttccgttg tcatccctct tacaaaggta tcaccaatgt aggtgtcatt ttatcttctg   7260
gcttgtaatt atctgtctct gttcggagac ttgttgtttt cagccaaggg cagcgctaag   7320
acaaccagca aacccagagt ttctcagcaa agagaaaact ctatatttta gtctttgttc   7380
tctagctgct aagtgtagat tttgtttatt ctgagaatta ttctgaaaat catttgctcc   7440
aagggccaat gccctctgca cagtagaggt cagcacttct ccaagtgtgg tccagaggaa   7500
gctggaggta aatgtagatt ccctggtccc acccaccctt atagaatcag aatcttgagg   7560
gggtggagtc ttggggaacc tgtattttcg acaagctcct tatggattct taagcacatt   7620
gaagcttaag agtcagtgaa ctagggcgaa acttttctta gagggatggc aaacacaagt   7680
gcctacagag acccggcagg aaatgcaaat gatctggaag aaaagccacg gcgtcatgat   7740
aaactgcacc aggacacttg gtcttggggt caagaagaaa gtagggtgtg tgagacaggg   7800
agagggaggg gacctggagc ccacgtgccc agccaaagca gcagccagcc tcagttcttg   7860
ctgggttttg cattgaggac tgtgggtcca gcttgattag ttcttcccgt gtcccagaaa   7920
agcagaaaat ctggatcttt ctgtgaagtg ttccaatttt taacatgggc ttaaaatgtt   7980
tatgggcttc taactcaaaa tttttaaagg tgttccatca gcgaaacaac atgtctaatt   8040
catttaacgg ttaatcaata gaaagctcac accattaaag cagtggtttc tcaaacttcc   8100
agaacatcta gaagccatgg tgccctttgc aacacattat aatctgtggt tctcaaccct   8160
ggctgcacgt tagaatcatc tggagatctt gaaaaaaata tgccgtggac cccactcact   8220
ccagtgtagt cagaactgct ggggaatggg tccaggaatc atttgttttt aaagctttcc   8280
aggtgattct aatgtgcagc cagggtagag aagtacagcc acactgataa atatagtccc   8340
ttcactagaa ccagcagaaa tgatatatac aagcaaaggc acacctagcc acccaggtgt   8400
ctgaacacat tttaaaaggc agttaactaa acatggtcag ctatttcctg gtttttccat   8460
gcatactgta catgaatatt ctttgcttat gttttgcccc gttaaacaaa atagagaaaa   8520
tggcattcac caatatatat tttttctgtg caatggaaaa agttgctcaa gatttaattt   8580
gtaaaggtgg gaccccctag tccagctctc aataatacta gtgttctgtg aggcatggct   8640
taagaaccac aaactcgttt gcagtgggtc attgtctgag gcataggttg acactctagg   8700
cccatttagt ggaatcttgc catattttgt tgatgaaacc atcttcacca gatgatctcc   8760
cagatccctc ccagcttgaa gagtctctgc ttcaataaat gaggtatgtt cagaagacct   8820
gggttcaaac cccacctcca ccaccttcta gttatgtgac cttgggaaag acatttaact   8880
ttttgaggct cagttttctc atttgtcaag tgataaattt tacatgtttt cattcttctc   8940
aggggttgtt agaaggtcac atgaagtaat aaaaactcga caaaacaagg tggtgctatt   9000
acattttgct tatttatgta tacgatgatt cattccacag attacttaaa acatcattat   9060
tcagtgaatt tgattgtcaa gaagattgta tgtacatttt ctttgatctc ccaggcaatt   9120
cttttttta attaatttta attttaattt ttttgacaga gtctcactct gtcacccagc   9180
ctggagtgca ctggtgcaat ctcggctcac tgtagcttct gccttctggg ttcaagtgat   9240
tctcatgcct cagcctcccg agtagctggg gttacaggtg cccaccacca cacccagcta   9300
atttttgtat ttggagtaga gatggggttt tgccatgttg gccaggctgg tctcgaactc   9360
```

-continued

```
ctgacctcca gtgatccacc tgcctcggcc tcccaaagtg ctgggattac aggcatgagc    9420
cactgttctc ggcctttaaa atttttaatt ttaaataata gggataggtc ctccctatgt    9480
tgtccaggct gatcttgaac tcctgggctc aagcaatcct cccgcctcag cctcccgagt    9540
agctgaaata acagacatgt gctaccatgc ccagctaatt ttcgtatttt ttatagagat    9600
ggggtttcac catgttggcc aggctggtct caaacacctg agctcaagca atccacccac    9660
ctcagcctcc caaggtgctg gctgggatta caggcgtgag ccaccatgcc tggctgccaa    9720
ttcttcttct tcttcttctt tttttttttt tttttgagat ggagtctcac tctgttgccc    9780
aggctggagt gcagtgacac aatctcagct cactgcaacc tcgacctccc aggttcaagt    9840
gactctcctg cctcagcctc ctgaatagct aggattacaa gcatgcacca tcatgcctgg    9900
ctaatttttg tatttttagt agagacgggg tttcaccttg ttgcccaggt gccaattctt    9960
ttttaatcac tagcaattgt gtcctaagct ttgcttgcta gtgtcaagtt gcttgtgtca   10020
gctaacttct gagtgactct ggccaagacc ctctagacag ccatttcttc ctctgaagag   10080
ggttgcgcca catgactcct gatgtccctt ctaatcatgg gaaatctata tatcccagta   10140
atagaaaaat gacctttccc acctctttct tgaaacctta aaattctccc caggatgtgt   10200
tcatcctggg gagcagatta tgattgatag gctggaagaa accaaagagg acggccacta   10260
gggtgtcctg agaactctct tagctcataa ctttccccat ctcctggctt cccactgcct   10320
tgacccactc tgactgtctc accagcaagt gccattttcc atctcccttc tttttttct    10380
gagatggagt ctcactctgt tgcccaggtt ggagtgcaat ggcaccacct cagctcattg   10440
caacctctgc ctcctgggtt caagcgattc tcctgcctca acctcctcag tagctgggat   10500
tacaggcacg caccaccagg cctggctaat tttcatattt ttagtagaga cagggtttca   10560
ccatgttggt caggctggtc tcaaactcct gatgtcgtga tctgcccacc tcggcttccc   10620
gaagtgctgg gattacaggc gtgagccacc gtgcccggcc ccatctccct tctttttaca   10680
gcaaggtgca tgttgcactg acttaccctt tattcctctt gtagtcactg gagctgtgtt   10740
atttatttac tttattaatt tatttattta cttgaaacag agtctccctc tgttgcccag   10800
gctggagtgc agtggcacaa tcctggctca ctgcaatctg gacctcccga gctcaagtga   10860
tcctcccagc aggtgctatt gtaactgaag ccatatcaat aacagctcct tcaaaaccca   10920
gctctgttgt ccttgatagg gttgccaatg caagtagctt atccacattc agagtattac   10980
aaacttgtaa acttacacat tacttaacta tcactgattt ctctccttgg ttctatctga   11040
aatggtttag ggaatcgttg gcagtatctg ttctttcaaa gccaattatt aatcagggct   11100
tcattagaca gcattcacac atttgttttc ctaacatctg ttccattaat tttctaagaa   11160
ccagcgtcag gcccaccaga tggcaatttc cagaaacact cactcatcct ttcctgaaga   11220
tcagtagcgc atttgcttgt ttccaggcct ctgatccttc ctgccttgtc tgtgacttcc   11280
tcaacaaccc ctcggggtga ttataagctc attccagcca tgtccattat gtgtggaatc   11340
tgggtctatg agcttgaatt tcaacttcgg gctattgtta ccatttgtgc agaaagtttt   11400
tctctgggtg ttaatactgc tcagaccttg aggctgtcaa gtgtacagga gcagagaaaa   11460
gacaggctct ttctctttct ctggctcaga ggggtgggaa agagcattcg ctgcccacat   11520
cttgtggaca gggatgaaga ggccagcagg tgacagcgtc tggcatagca cgtgctgtca   11580
aggaaagaga aaggagccaa tggtgacaca ccagcttggt cagaggaagc atctgtgttt   11640
ctgccaggct catgatgtgg gctctttgct atataagccc tgctttattg ggtctaaaac   11700
acaaggttga gatgtcactg cactgctcaa acactttcag tgactcccta ctgttaatgg   11760
```

-continued gttaaaattt aacctttag tctgacaggt ggaccccaat ctatcatctt gccctttctc 11820
acctggctcc cacctgctgt ttcgggcccc tcttactcat ttgcatttcc tcccctccct 11880
gcctttgctt ccagcagtca ctccatgtaa catttctttc ctccccatcc tcaaatcctc 11940
tcaattttca ccccttccgt gaagtgctcc ttgccatttc cctcctttga tttcctgcag 12000
caactcctgg acttctctga aaaccactgg tttcctgtcg ctcccctcac ctgtgctcct 12060
gcattgtgac atcttccggg gcactctgtc ctattatttc tctctagtcc tgttatttgg 12120
gcccatgtat taatacccc ccttagatat taacccataa gcctgaggct gcactttttt 12180
gaattttgaa atcagacctt ggccttgacc ttgagcagca ggatataaat aactcttaca 12240
tgcttagcgt tccaataatg gaacaccagg cataaatggg ttttaatccc cttgaaggca 12300
ggggttgtgt ctactcatgt tttgcttccc aaggttagca ctatgcttgg catatagtag 12360
ctgctcaata catctttgat aaatgaatga atgcccagat gaacaaacac acgaataaat 12420
caactagctg taagatatgt aaactactag gtgctgatat ctttctagaa tcagtatttt 12480
ctcaaaaagt aggaaaaacg ggttggaaaa cttaccagaa ctgagatgtc aaggcagtgg 12540
gaggaggggg caattagatt tgactggcca gtctagtgcc atgttgtgga gctctgaggc 12600
cacactgctc cttgctcagg actgtgtgtg attctagggc caccaagaat cttcctcgta 12660
tctccacctt gcggtctgag gcctcaagcc tctagggagg tggcaggcgg gacggtggcc 12720
acttggtgcc tgtccgttgg cagcacactg ttcctgcatg tctcgctcat gctgtgccct 12780
ctgctctgct ttatctccta gacgaactgg ctgtctgccc taaaggaatt acctccaagg 12840
ttttccgctt caatgtgtcc tcagtggaga aaaatagaac caacctattc cgagcagaat 12900
tccgggtctt gcgggtgccc aaccccagct ctaagcggaa tgagcagagg atcgagctct 12960
tccaggtaac tcctctctca gagcagaaac cacaccgacg ggaaagctgg ttcctttgcc 13020
atatcagggc accactgggt gcagcgtttg gcagacctgg gtttgaatcc tggcttctct 13080
gagccttcgt ttccgtatct gtgtctgtca ttaaaacact taagagttag ctaaggtgct 13140
cgagggccat ggcattcagg aaccactggt ttcctatcgc tccctcacct gtgctctgca 13200
ttgtgacatc ttctggggca ctctgtcctg gtctcgggta ctcactcctt tctctgccct 13260
gtagatcctt cggccagatg agcacattgc caaacagcgc tatatcggtg gcaagaatct 13320
gcccacacgg ggcactgccg agtggctgtc ctttgatgtc actgacactg tgcgtgagtg 13380
gctgttgaga agaggtaggt ggacccttca gataagcatt tcagaatgaa cctcaggtcc 13440
cttagtcctc catgaaatgg agggaagagg acagaattaa gggagtcaga gatctgggtt 13500
caaaccctag ctttgccact gagtatcctc cattcattca ctcaactaat gtttattaaa 13560
tgctcactgt aagacaggcc ctggggatgc agccacaggg ataggaacta tgagaaatag 13620
aaagagggca atgtgacaat gagtgggtgg agtccaacag ggaaggtctc tatgatgaag 13680
aaattcatgc attgacatct gaatgataag gatttagccc atgaagatca gaataaggga 13740
tgtgctaagc aaaggcaaca gggaggccca ggccctcaag tggaaataag cttgatttgt 13800
tctagcagca gcagcaaaca gatcggtgtg gctggagcat ggtgagctgg ggaggggaag 13860
aggaggggag gtggtcaggg aggttgctgg ggccatataa tttattatta ctattattat 13920
tattattatt attattatta ttattattat tattatttct tgagactgag tctcgctctg 13980
ttgcctaagc tggagtgcag tggtgcgatc tctgctcact gcacctccac catctgggtt 14040
caagcgattc tcacgtctca gtctcctgaa tagctgggac tacaggtgca cgctgccaca 14100

-continued

```
cctggctaat ttttttgtat ttttagtaaa gatggggttt caccatgttg gccaggctgg  14160
tctcgaactc ctgacctcaa gtgatccgcc cactttggct tccaaaagtg ctgggattat  14220
agatgtgagc cagcatgccc agccaattta atttagaaca tcatcaggtc atggcgaggt  14280
ttcaggactt attccaggtg tgatgagaag tgtgggagtg ctataaccag agctggggat  14340
actcaagata cccaggaatt ccttcctgtc cctctactgg gtgtgaagtc aagagcctag  14400
gagaacccac gtggatctgc caacggcagc tctgttggga attctgactc agacagctac  14460
agggaggagg ggctgggtga ggtgatttga ttgacatctt taaaagatcc ctctagtttc  14520
caggaggtca agggaagagg caggaaaatg agttaggagc cacggcggca gcccagatga  14580
gagcaatatc taggccgaga ctagggcggt agcagtggat atgacgatca gatggatttg  14640
ttctgtattt tgaaggtagc cagtagcaca ggctgattag gtatgggatg tgaggacaca  14700
agagcattcc agataacttc taaatttttt cgacatccag gtggtatcac ttattgaaat  14760
agggggccta ggagaagaac aggttctgtt ctgcccagtt aagtttaaaa ggccgggtcg  14820
tcatgcaagt agagctatcc tggaggcata tcaaacttca catgtcccaa atatcttacc  14880
cacacactgc cttcacctgg aaaatcaggc aatggttcct cctctatgta tgcctcacag  14940
agctgtttta aggatcaaat gtatttgaga gaacttcatg gtttttacca tgttttacaa  15000
gagtaagctt ttcttatttt agataaggaa acaggccgag agaagttaag tgacttgacc  15060
gaggtcgtcc agtctggatt agaactttgg tgtctcatga caccatcctc tgtgtttctt  15120
tccctttctt tggctggtac tgcctggtct gatgctcagt gggttggggt cacagatggc  15180
agtcccatct gttccttctc ttcctcttgg gcaaggtttt ctcctgtcat cagctgctat  15240
aaagccacag accatccaca tattgatgcc cagagtccct gaggcaggtg gatccttcta  15300
agtccttggt gttttaggca actaagagtt aaagctcaaa ggcagagctt acaaactatt  15360
tggcctgcac attgttttcg atttgactag tcatcaacag ttttgggtgt tttaagtcag  15420
gagatttcac ataaaacctg gacttcttgc tgtttttgaa aaatcgaaag atttcctgat  15480
aaccatccgt cagagatgag taccggccac cccttgagat ggggtatgca tcctcagtcc  15540
ccgcagcccc caccattccc tattgttccc caagagtgag gctggcagtt cctgtttagc  15600
atcatgtgct ggctcgattt tctcacttac gtgacctgcc tgggctcggt agccatcgag  15660
tttgcattgc ttgatgccac ggagcccagg caagtcacat aaatgagaaa attccccatc  15720
caaggggaat tatccagtgg ctgagttggc agatggtggg ctgaagatcc tgccccagtc  15780
ccaagggtac ccaggaattt catcctgtcc ctcctactga gcatgaaggc aagagcctag  15840
gagaacccac gtggatctgc cgacagcagc tctgttggga attctgactc agacggctac  15900
agaaaggagg ggctggggaa attaatctct taacttccct gtctgatttt gatcagctcc  15960
acctggattt ctttgaagcc ctgggcactt gaaggagttc ttattttcac agctgcagaa  16020
ctcaatgaga agtttgcatt gagaatgatt tccatcctcc tgagacatca aaaagataat  16080
ttcgtaataa aacctatggg tcccccaccc accaccccca cagctgccaa ttctgaggtt  16140
agttcttcat tggaaccttc agttcacact taggcagata ctgcccacct ttcccacagg  16200
ggaatcatca cacaggtttg tacttacaga gagcccatga gtctcttcag agttcatggc  16260
ttcaaaccag gcaacaaagg actccaaatt ggagcagttg gcggtgtaga ttgatgagaa  16320
aactgagtca cacatgtggt cttggattca ttcagcaaac atctgagagc ccttgtgcac  16380
caggtaccca ggctgcattc tgggtcgcag agtgggttgg agtccacaag ggccgctggg  16440
gacccaggtc tcataccctt gtgctattgc tcatatagtc tgcagcacct agctaggcag  16500
```

-continued

```
ggccaggcct cccctagtag gctggggagg gagcctctca gcatcatggc tcaggaaagg  16560
tgggacactg ggaaacaacc atcttgcatg ttggtgaatg tgtgggcatc ttccttggtg  16620
gtctctgttg ccccctcttt acccctcctt gtctctaaca agagtttggg atctggcatc  16680
aagctgtcag tgcttgaatc ctggcactac tatccactgg ttggatatct tgggcaagct  16740
gtttaatctc cctaagcctc agtgttctta tctgtacaat gggggataat agttcttgct  16800
ctatgggatt attatagaga tagaataagt tagtgattgt tgtcatcatc tctaagtcct  16860
ctatctggat acagcctgtt ggccaagcca ggccaccctc ttgtgcttac atcctggacc  16920
ctcactctcc ccaacacagc tgtctgcacc ttgactttct aactcacaga atcatggaac  16980
tcactcactc caggtctctt ccagcctgcc ttgaaccagc ttgaccagga ggtacactgt  17040
gttgttaggt agcccatttc agctactttg gctcctcctt ccagctgcct taacccaggg  17100
agagggcaat cctcatacct ccctctccat tcacttctcc tccagctggg tctcagctgc  17160
cttgttttat tggtctgcct tccctcactg agcgaacctg ctggaacaga gatcttcaag  17220
ctcagcaggc gcagtgtgcc tcagaggttg ccctgactta gggtagagca gatctggtta  17280
ggctctggag tttatggaag aaaggagctg ggttttaacc agtaggactg ggatgtccaa  17340
gccaacctaa tgttgatggg aatctccagt cttgtaggct tgtatccttc tgtctatgag  17400
aaggttgctg ggccaggttg gactttttgg ggtttgccct gatggcacaa tttcaggaag  17460
actccaggtt gtctccaagg ccagatgctc acacacatgg tgtgtggcct cagggagcag  17520
caaatcaatc aactcatcga gaggctgacc ctgaatccag agaggtccat cccccatgac  17580
ctctcctaca cctggccaca actggctgct atcccaggat caacagagct tcccaaatta  17640
agtcttaccc accagaattg acatgatacc agatcctacc tggttttctg tgtaaaacta  17700
cttgtctcag tgcagacttt tcattttctt tctttttcct tcacttcact caacctcatt  17760
tactgagttc ctgcttcctt gattttggtt gccaaaacat gtgatcccac aactactagg  17820
cgaatgggct ggagttgccc ttcacgcacc agaatgtcag gcaccaaacc ctggcacctc  17880
caggcttcat catgctcact gtctccgtgc tcaagtcatc tggaccctca gccatagttc  17940
tctatcatct cctctgtgct gttttctaag ttcacaactg tcttcccaag ctgttcatct  18000
tggtgagcaa tccacattcc aacttcccat catggtgaac aaggattccc aaagaagaaa  18060
tgtccaagta atttttacct cgttgtgtcc ttgttcctta ggaaaaatat ggcccagtgt  18120
aaccgtgatc ttcatcttat ctcttctaga atctgccact ttgtctaggc ccacagtcat  18180
ggccctggta gaaatgcttg catcttccac tgagacggat tctgcttcct gtttgcaagt  18240
gaccttgcct ctagcattgg ttcctgactt gaatcttttt gccagcatta catcctgtgg  18300
ctttttgaat ttgtggcctt ttgaatcaca gtctctgtgc tcggagactc tttagttact  18360
ccctgtccgt agtctcttcc agtccctctg cctcttgccc tgatccttct gcagtagatt  18420
ggctcaacga tcccctctcc caaaaaccat gtagatggca tgagtttttg ctttccttac  18480
tgtatctgtg tacttttgcc tccaagtagg taggtgacaa ttttctctta ataccatcct  18540
ttcaaaggga atgattattc cacttctgtt tcatgatggc cactagtgta tgcccccatt  18600
tggtgattca taatacaaca ggaatacctg gaatgtggca acgtgcgctt gaaggtccac  18660
tctgagctct ggaggcactt tctgtctcct gtgaccctca atagaactca gttcctatga  18720
gtccctatag gagcagaggc cctggctcac ccttgcatgg gtggtgggca cacttcccca  18780
tcacacagag gtgcttttct cactaattct gtcttatttt gcagagtcca acttaggtct  18840
```

-continued

```
agaaatcagc attcactgtc catgtcacac ctttcagccc aatggagata tcctggaaaa  18900
cattcacgag gtgatggaaa tcaaattcaa aggtaacaaa atgaatgtgt atggtaggat  18960
gggtgagtgg gggggaagtt aatgggacag gatagtgcag gagaccctta ccagacctca  19020
agaaaagaaa ccaagctcct tcagagagat agccgactat tttgtacttg agtaattctg  19080
ctttgcccca aaagcaatga gtgtaacttt cagtttatag cttagagaat gcattagcct  19140
ctggaagaca acacgtactg gtaagtggtg aaactgtgta ggcaagccat ctagcctctg  19200
gtcctagtga aatgggatga gagttcctct ttcacagtgt tgtcaggcaa ttaaatgaga  19260
taatgaataa ggaacacagt gccagaaatg ctcaacagat aggacttgtc ttcctcctcc  19320
ctaaaagaaa ttaagtttgg ctgtcctgaa catgagtgcc cagacaactg agctttccag  19380
atgtgcaggg cctacctgac cttgcccagg ggtcctctgg gtttggatga ttgcttcgag  19440
cctcagggtg tttgtccccg gggtgtttgg gtagagatgg cgaagtcgtt gagagtcatt  19500
tctggttttc cattatgttt gcaaggaact cagccttgat gatctctgga gttcagggaa  19560
gttctctttt cctttcatat tcccattttg ggtaactgcg gaacgcctga ggtcagaggc  19620
ttgtctggga aaaggtgcag gcctcttttg gctcagcgct ggacagtgat cttaccccac  19680
atgggctcta ttttacagcc ttttcttaaa gccaaagatt tgacactgta accacagaac  19740
cttagagccc agaggacctt tggagtcctt acctacaggc cagcttagga tgaaaccttc  19800
ccatttcagt gaatacttat cttgttcata aagattttca gaaaaaggga tttgtgatcc  19860
aggtctctca tttatcttac agatctggtg ccccttcctg agacccgagc cactcctgta  19920
gctatgtaaa ttaattcctc atgttcctgt cctcagtgag gatggacaac agttggcagc  19980
tgtccttcgc aaaatcgatc tccatttagt tgagactctt tctaagtcag tctccagtct  20040
tttccttttt tttcagatga aacgggttga tgaatttaga ttttctttcc agagcttatt  20100
tgctatttat catatgcttc attatctcat ctgaatttta tagtgaaaac acttcaaaga  20160
ctctaagtgc aatgtgaatg ttaacaatta tacagtcttg tttctttggc tcccattcag  20220
gctatcttaa gttgtgacac cttaaatttt tggtaggact tctgcgttat cttggtccat  20280
tcacatttta agaggaaact cacaccccaa gattctaagt ctagaatcta aagtgacaat  20340
ccagggctgg gtgcagtggc tcacacctgt aatcttagca ctctgggagg ccgaggtggg  20400
cggatcactt gaggtcagga gttcgagacc agcctggcca acatggtgaa accctgtctc  20460
tactaaaaat acaaaaatag ctgggcatgg tggcatgcac ctgtaatccc agctacttgg  20520
gaggctgagg caggagaatc tcttgaaccc cggaggcaga ggttgcagtg agccaagatg  20580
gggccactgc actccagcct ggccaacaga gcgagactct gtctcaaaac aaacaaacaa  20640
acaaataaac aagccgacaa cccggagata tgtgttaggt acccacttag taacagggat  20700
gcttcatagg tccatgaaga ttcctaggaa tctcagcaag ggctttctgc cccttggaag  20760
atttctatac aagggtatgg ggatctgaac acggggcatc tttcagtggg catccttaca  20820
ataataatga gttcttttga tactggcttc tccatctgct cttccccttt ctgcacctgg  20880
acatcagaat taagctgcac ttgtccccca cacctccctc gcagactgca ctgcccctcc  20940
tcctgggcag tgatggggcg tgtggaggag gcagcctcca agggctctgc tctcttcaga  21000
caggagattg tcactttcct tcccttcttc aggcgtggac aatgaggatg accatggccg  21060
tggagatctg gggcgcctca agaagcagaa ggatcaccac aaccctcatc taatcctcat  21120
gatgattccc ccacaccggc tcgacaaccc gggccagggg ggtcagagga agaagcgggc  21180
tttggacacc aattactgct tccggtgaga ctgggcccac atgggaacca acatctactg  21240
```

-continued

```
cctgcctact gcccaatggc taggtcaggc cccagagcca agccacactc aacagagggt  21300
ccctgatgct attcacaaac atctccagga agaagactga aaatctctca cagagatttt  21360
ctctgtgaaa tctctttctg ttttcctggg agtcccactg tttttccata ggctaactct  21420
ggaaggagct ggctgaagta aatgaggaaa actctgtgag gaggagtgtt gctaaaatag  21480
tttggattgg agaggcttgg tcaaagcctc tccatgattt ccatgtttta agcacttgta  21540
gagtgtatgt gtgagattaa tgtaggagtt tccattaaag aagtgctcag ttagttccct  21600
atgaagggtc caaggatgct actggatgga ggcaaataga atggtctcca tttgaacgga  21660
aagttggagc tagagaaatt aacaaatgaa ttcagaaatt actgggtagc cacaatagag  21720
agatagaaaa gacccagctt ctcttactca ggagcagttt cactgctcat ttataaaggg  21780
aggataaagt atgcatgcca actactaaaa gggagaagat gatcacgccc atgagagggt  21840
ccgaaggatt aagtgcttta actgggagca atgagttcac ctatggacac aggaaaggct  21900
tcagaagggt gtggaatttg agcagaggct tcaaggatga ggtttgggga tgaagggatc  21960
caggagggga agcactgcag gtaaaggaag gagcatgagt gagtgagtcc atctggcctc  22020
agaggatgcc gaaatgaagc tggggagaac gaattgggaa atatttagat ctggaaacca  22080
tgtcttatga ggatggttgg gcttgggaaa ctagggatgt tcagttgggg gaacagctca  22140
acagcaaggt ataggagagg caaggtagtt gccacaaagg ctggcatgta gatttattta  22200
ttccatcagt taggaacaaa tcagttagga acgaatcagt tatcagttag gaacgaatca  22260
gttaggaacg aatgatcttg gccagtgact ttaatcatag tgatttcttg ttcacaagag  22320
gcctgtagca gcagggttag ggtgggctgg ctgcttaatg atgccaccga agactcaggc  22380
tttctctctt tccagtctgc catgcttagt atgttggctt ttcatccttt tccttatggt  22440
cacaagtgat tgctagggct tcaggcacct tgtccacatt taagacaaga aggaatgagg  22500
gaaggggaag agccagaagc tttcttcttc catctgtcac ttttataaat aatcgaatat  22560
ctttgccaga acttgccctt accccctgca tacttctcct tgtctgatgg gtcattactg  22620
ggtcacatga ccaccgctac tctcaaggga ggacaggaaa aggagcatct ggtgttttcg  22680
actctgtaat gggatgtcac aagggagaag ggagttagga atggttattg aatagataac  22740
caatggtgtc tgccatggtt caccccttgga acccacaaga agccagattt tggctaatag  22800
ctgcctttgg aagtagcaag ttctaagtct cagcagatat taaagcagag gctagctgtc  22860
cacttggcaa gcggtattat tgccaaatga tctctgtagg caacagaatt gaaggggcct  22920
gataatcaca tttgggtgat ctgttgaacc acggttctaa tagaaggata tgccttattt  22980
ggctaaatgg cctttggatt gagtctcagc agtcacctac tatagtagtc aagctgcata  23040
aacttagaat tgatttctgt ctgggtgcac attaggaggg taaaaataaa accaacctca  23100
acaaagctga gttggctaat aacattcagt gcttggtttt atgtggagcg cttcatagca  23160
ctgctttgta ttgtgataga aaagggtgca gggccacctt tgcctcttta ctcttcctca  23220
tgcagcattt atctctgttt cttacatcct tgggatcctg gtctttaaca catgaatgtg  23280
cctttctggt ttcttctgcc ccatgccctt gaacctggga ttccattgat cagagccacc  23340
tatgatggca tgaaaggact ccaagggaga atatgagagc attcatgaag tttcttttat  23400
tggtggtttt aagttgattt tctataaatg ttttttgttg tagcaacttg gaggagaact  23460
gctgtgtgcg ccccctctac attgacttcc gacaggatct gggctggaag tgggtccatg  23520
aacctaaggg ctactatgcc aacttctgct caggcccttg cccatacctc cgcagtgcag  23580
```

-continued acacaaccca cagcacggta tggagcaggc tcatgccatc tgaggcactg gggctgaccg 23640
accagaccac ttgttaaaaa gaatgagtga aggattgaat gttgagtgag caaatgatgg 23700
tctggggtga gtaaaattcc tctggtgaag gttctgatct tggcaccctg actcagttct 23760
actcagtcac attctgccct tttaaattcc taccatagtt tcaaccagct ttttaatttg 23820
ctttgtccaa agctctctgt accgtagaaa ttaattaact gccacgtgtt accctatgtc 23880
agagatatgt gcatgtggct ggcaaggaac actgaagtag aaaggcttct atcagaactc 23940
tgatcattcc agcctctcga atgtagaaaa cttactctga aagacaacaa caaggatgga 24000
caagaagcta atttgaaatg ctaggaacag aaagtgagat agccgagagt ccacaacccc 24060
tgaaactagt ctgtctttcc cttgagggga atcaaaaata gggcagtaat ttgtgaagca 24120
tgtttccttc tagctcattg tttctgcatc ctgtctgggg ccctgcacgc tgcacttact 24180
aaatggctca aggcaatgtt ttgtgagaac atttctcacc gaagtgatca gttccagcta 24240
ggaagagcaa tgtaagtgtt ttcttaaaag ccaagatagg ccgggcacgg tggctcacgc 24300
ctgtaatccc agcactctgg gaggccaagg cgggtggatc acaaggtcag gagttcgaga 24360
ccagcctggc caacatggtg aaaccctgtc tctaccaaaa atgtaaaaaa ttagccgggt 24420
gtggtggcac gcgcttgtaa tcccagctac ttgggaggct gaggcaggag aatcgcttga 24480
acccaggagg cggaagttgc agtgagccaa gattgcacca ctgcacttca gcctgggtga 24540
aagagtgaga ctctgactca aaaaaaaaaa aaaaaaaaaa aaaaaaaagc caagataatt 24600
cgttatcagt gtagtaactg tcatatgctt caactcatca ccccaaacaa gtgcagttgt 24660
tctgcttctg tcattgtgga tgaacagcaa ctacacaact actcactcac ccaaaccagg 24720
ttccaacagt tttttttttt ttcttttttt tgagacagac tcactctgtg gctcaggctg 24780
gagtgcggtg gcactatttc tgcttactgc aacctctgct tcctggattc aggtgatcct 24840
cccacctcag cctcccaagt agctgggatt acaggcgcct gccaccacag ccagctaatt 24900
tttttgtatt tttagtagag atggggtttc accatgctgg ccaggctggt ctcaaactcc 24960
tgacctgaag tgatctgcct gcctctgcct cccaagtcct gggactacag ctgtgagcca 25020
ctgcacccgg cccccaacag ttcctcttaa agagcacccg tggccattct agcacttgct 25080
cagcttctgg gactgcccct ggaactgggc gacttcctgg gttccaggcc tgagacttgg 25140
ccttccaacc tctcactgac atgtcccttc ccaggtgctg ggactgtaca acactctgaa 25200
ccctgaagca tctgcctcgc cttgctgcgt gccccaggac ctggagcccc tgaccatcct 25260
gtactatgtt gggaggaccc ccaaagtgga gcagctctcc aacatggtgg tgaagtcttg 25320
taaatgtagc tgagacccca cgtgcgacag agagagggga gagagaacca ccactgcctg 25380
actgcccgct cctcgggaaa cacacaagca acaaacctca ctgagaggcc tggagcccac 25440
aaccttcggc tccgggcaaa tggctgagat ggaggtttcc ttttggaaca tttctttctt 25500
gctggctctg agaatcacgg tggtaaagaa agtgtgggtt tggttagagg aaggctgaac 25560
tcttcagaac acacagactt tctgtgacgc agacagaggg gatggggata gaggaaaggg 25620
atggtaagtt gagatgttgt gtggcaatgg gatttgggct accctaaagg gagaaggaag 25680
ggcagagaat ggctgggtca gggccagact ggaagacact tcagatctga ggttggattt 25740
gctcattgct gtaccacatc tgctctaggg aatctggatt atgttataca aggcaagcat 25800
tttttttttt tttttaaaga caggttacga agacaaagtc ccagaattgt atctcatact 25860
gtctgggatt aagggcaaat ctattacttt tgcaaactgt cctctacatc aattaacatc 25920
gtgggtcact acagggagaa aatccaggtc atgcagttcc tggcccatca actgtattgg 25980

-continued

```
gccttttgga tatgctgaac gcagaagaaa gggtggaaat caaccctctc ctgtctgccc  26040
tctgggtccc tcctctcacc tctccctcga tcatatttcc ccttggacac ttggttagac  26100
gccttccagg tcaggatgca catttctgga ttgtggttcc atgcagcctt ggggcattat  26160
gggttcttcc cccacttccc ctccaagacc ctgtgttcat ttggtgttcc tggaagcagg  26220
tgctacaaca tgtgaggcat tcggggaagc tgcacatgtg ccacacagtg acttggcccc  26280
agacgcatag actgaggtat aaagacaagt atgaatatta ctctcaaaat ctttgtataa  26340
ataaatattt ttggggcatc ctggatgatt tcatcttctg gaatattgtt tctagaacag  26400
taaaagcctt attctaaggt gtatgtctga ctcgataaat atccttcaat tacccttaat  26460
tccatgtccg catctactaa tcagaggtaa ccagaatctg gggcagagaa tctgtcaatc  26520
accaaacaca ttgcttagcg caactcccct tacacagggg gcacaccgtg ctgacttccg  26580
cctgctaaga agactgcact attgcttgtg cgtctttcct tcttgcagag tatattattc  26640
tcagagacac agaggcagtg gctcagattg gcagaaagca catacgaatt tgacctccag  26700
atacctgtgg gcaggatccc ctggtgtgaa tccttgcata tggaaacatg gtttatttac  26760
taactataaa ttaccaacat cactgttttc gaaaatctcc ccccacccgt atcagttgag  26820
aatgagagaa aatgtgtatg gcaaatggcc taaaaatatg aggctaattc tgttctcagg  26880
ctaagcctaa aagagctaac caggaacccc ttttcagatt gtggccctct tgtcagggat  26940
ctgggaacca tagctctctt ttgagtgagg ccgtggatcc cactgtggta tggacatcca  27000
cgtggggcag ccgtccacag tgagcgggca cagagcgaca ggccatctag cagctcctga  27060
gaaacacatt cttctagtga gatcactttg cctctagtaa aagaaaagtc tatctgaagc  27120
taaagtatgc aggctgaagg atgtgtctga tgtgttcatg cctgtgtgtg tgtgtacgta  27180
tgtgtgtccc ttgttccttg agttctccaa gactgaagtg agtttggtca gtactttttt  27240
ccccgctttg tccacgccca gccaattcta agggtttccc tctcagtctt catcccatgt  27300
ggcacccact gacttccacc atcgttcgga gggctatgtc cctgtcctaa aatcctggct  27360
ggcgggatta tactccatct tgctccaggg agcccggggg cacagagagg ggatgcagta  27420
agctcagcac atcagccacg ggctgctgct gtcccagcat cagtctattc acctgagggc  27480
cattctcaaa ttcactgggc atgataaccc ccaagggttt atttaaaatg tacagtttca  27540
ggctgcagct ctagaggtac ctttaggact gcagtagggt ccaggttgcc tcaaaactat  27600
taacacattt tgagaagtgg tgcattacac ccgacatcac tcgtccttac ttgaggcttc  27660
aatatagaaa agggaaataa tttttttggc cccagatgaa accccctttt atccaacttc  27720
acagcacatt gctaaaacat tggcctgtgg ttcatcctaa tgaaccaagg cagctagata  27780
catttcctgg attattccaa agaaaacaga acgtggtgca attccaaatg gtctttttct  27840
tcagagctct acttgtaggt taggcagcag acacaaatac ggacaggggt ctgaagtcag  27900
cccccctatt ctacacatca ctgacaggtg ctacagaaac ttgaatcact gtcttcaaaa  27960
atcgacgctt gttttggggg agggtaaaga gtgacattgg aaatatcacc tctgttggag  28020
gagggctcat agcatctgtc tggtttattg ccaagtgaag tccagtccca ataaaaatga  28080
cttgaaagca cttggacaca tgaagggaga gatctggtgt cttagcacct gatcagcata  28140
tggtaagtgc agtaagaaat tagctggaag acttcattct gattggttac ctagggcaat  28200
ttcaagcatt atagtctaaa acttctttta ctgggctcat acttttttcc cttgtcacaa  28260
gattcacgtg gtgagtcctc ccaaacccct tatttcccaa ttctacacct catcagggga  28320
```

-continued

```
ctatggagga attctaattt gtcccctaat caactcacaa ccaattgagc aaatagttaa  28380

ggtggtcctg aaactactct ccagtcccgg ggacatttgg aatgcattct tacttctctt  28440

ctgaaaccca tagacctcat ccttcacaag caaacaaaat gtgtccatgt gcccaaacct  28500

ttgttttcat tcagtaagaa ggcaataaag tcccttttct gcccttttag gtgtcaattt  28560

tttctttttt tttttttttt tttttttttt caggtggagt cttgctctgt tgcccaggct  28620

ggagtgcagt agcatgatct cggctcactg caacctctgc ctcccaggtt caagcaattc  28680

tcctgcctca gcctcccgag tagctgagat tacaggcgcc tgccactgcg cccagctaat  28740

ctttgtattt ttagtagaga cgaggtttca ccatctttgc caggctagtc ttgaactcct  28800

gacctcgtga ttcacccgcc tcgacctccc aaagtgctgg gattacaggc gtgagccact  28860

gcgctcagcc aggtgtcaat tttctttttg gatttcaaca ctgagtccat agtaccctgc  28920

tgaagaagcc ccagagcctg ggttctcccc tgataactct ctagggcagc taagttaatc  28980

cttcagtgga ctctgctgtc                                              29000
```

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
ttgttgtcca tgtgtctaaa 20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
ttcaggactt ccaggaagcg 20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
aggtgcatga actcactgca 20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
cggcaaggcc tggagaggaa 20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 22
aagtgcatct tcatgtgtga 20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
tttgcaagtg catcttcatg 20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
agccctttgc aagtgcatct 20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
accagagccc tttgcaagtg 20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
aagttcagca gggccaggac 20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
aagtggacag agagaggctg 20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tgcaagtgga cagagagagg 20

<210> SEQ ID NO 29

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
gtggtgcaag tggacagaga 20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
ttgatgtggc cgaagtccaa 20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
tcttcttgat gtggccgaag 20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
cctcttcttc ttgatgtggc 20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
tccaccctct tcttcttgat 20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
tggcttccac cctcttcttc 20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35

-continued cctaatggct tccaccctct 20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
tgtcccctaa tggcttccac 20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
agatctgtcc cctaatggct 20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
ctcaagatct gtcccctaat 20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
ttgctcaaga tctgtcccct 20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
ggacgtgggt catcaccgtt 20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
atcatgtcga atttatggat 20

<210> SEQ ID NO 42
<211> LENGTH: 20
<212> TYPE: DNA

-continued

<213> ORGANISM: Artificial Sequence
<220> FEATURE:
<223> OTHER INFORMATION: Antisense Oligonucleotide

<400> SEQUENCE: 42
ccctggatca tgtcgaattt 20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
tccactgagg acacattgaa 20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ttctccactg aggacacatt 20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
atttttctcc actgaggaca 20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
tgggcacccg caagacccgg 20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
gtgggcagat tcttgccacc 20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
cgcacagtgt cagtgacatc 20

-continued

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
aaggtgtgac atggacagtg 20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
gctgaaaggt gtgacatgga 20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
attgggctga aaggtgtgac 20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
tctccattgg gctgaaaggt 20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
aatttgattt ccatcacctc 20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
tctccacggc catggtcatc 20

<210> SEQ ID NO 55
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 55
ttgcggaagc agtaattggt 20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
tgagcagaag ttggcatagt 20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gggcctgagc agaagttggc 20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ggcaagggcc tgagcagaag 20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
gcactgcgga ggtatgggca 20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
tcagggttca gagtgttgta 20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
gacttcacca ccatgttgga 20

-continued

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
gggtctcagc tacatttaca 20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
agtgaggttt gttgcttgtg 20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
gaaacctcca tctcagccat 20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
agagttcagc cttcctctaa 20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
ttagggtagc ccaaatccca 20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
agccattctc tgcccttcct 20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 68
tcagatctga agtgtcttcc 20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
tccagattcc ctagagcaga 20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
gtataacata atccagattc 20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
aaaatgcttg ccttgtataa 20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ctgggacttt gtcttcgtaa 20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ttgcaaaagt aatagatttg 20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
ttaattgatg tagaggacag 20

<210> SEQ ID NO 75
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 75
ctggattttc tccctgtagt 20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
aactgcatga cctggatttt 20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
atacagttga tgggccagga 20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
atccaaaagg cccaatacag 20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ccaccctttc ttctgcgttc 20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
gtctaaccaa gtgtccaagg 20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81

-continued

```
tgcatggaac cacaatccag                                                  20


<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82

atgccccaag gctgcatgga                                                  20


<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83

aatgaacaca gggtcttgga                                                  20


<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84

cacctgcttc caggaacacc                                                  20


<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85

tgtagcacct gcttccagga                                                  20


<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86

agtcactgtg tggcacatgt                                                  20


<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87

agtaatattc atacttgtct                                                  20


<210> SEQ ID NO 88
<211> LENGTH: 20
<212> TYPE: DNA
<213> ORGANISM: Artificial Sequence
```

-continued

<220> FEATURE:
<223> OTHER INFORMATION: Antisense Oligonucleotide

<400> SEQUENCE: 88
atatttattt atacaaagat 20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ctgttctaga aacaatattc 20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
ctgctggaag caaaggcagg 20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
gaggagttac ctggaagagc 20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
gtccacctac ctcttctcaa 20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
atgccatcta catggttttt 20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
ttgtccacgc ctgaagaagg 20

-continued

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
ccagtctcac cggaagcagt 20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
gctgggcggc cgcaggccca 20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
aatcaccagt gggtatgtgg 20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
ctgcttggcg aggagaaagt 20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
tatctgatat cgcccaacgc 20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
ggatatctga tatcgcccaa 20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 101
tctgactccc agcaggccag 20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
taggatcctt gtccatatgt 20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
ccctggacga agtagcggga 20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
gctggcaacc cctggacgaa 20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
tgcgctgggt gagcttcagg 20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
ggagacccca gtagaaaggg 20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
caaggaggag accccagtag 20

<210> SEQ ID NO 108

-continued

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108

catcttcatg tgtgagccca                                                    20


<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109

gggccaggac taccagagcc                                                    20


<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110

gctgattgtg gccaagttca                                                    20


<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111

cagagagagg ctgattgtgg                                                    20


<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112

atctcttcca gcaactcccg                                                    20


<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113

ccgtgcatct cttccagcaa                                                    20


<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
```

-continued gactccgagg tctcctgagt 20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
actcagactc cgaggtctcc 20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
tcattgtgct ccgccagtcc 20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
ttggactctc tcctcaacag 20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
acccaagttg gactctctcc 20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
gatttccaga cccaagttgg 20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
ccagtatgtc tccattgggc 20

<210> SEQ ID NO 121
<211> LENGTH: 20
<212> TYPE: DNA

-continued

<213> ORGANISM: Artificial Sequence
<220> FEATURE:
<223> OTHER INFORMATION: Antisense Oligonucleotide

<400> SEQUENCE: 121
cacctcatga acattttcca 20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
cccaggtctc cacggccatg 20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
ccttttgctt cttgagacgc 20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
tgtgggttgt ggtgatcctt 20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
atcatgagga tcaggtgtgg 20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
ggatcatcat gaggatcagg 20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
ctgggctgtc cagtcggtgt 20

-continued

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
ctcttcttcc tctgactgcc 20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
attggtgtcc agggccctct 20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
tctcctccag gttgcggaag 20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
ctgccggaag tcaatataaa 20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
catttccagc ctagatcctg 20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
accgtgctat gggttgtgtc 20

<210> SEQ ID NO 134
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 134
tccaagcacc gtgctatggg 20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
acgcagcatg gcgaggcaga 20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
ggctggcctc agctgcactt 20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
gtggcagttt tccctcctct 20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
agcagcagtc tgtggtggca 20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
tgaggtctgt cgctttggtt 20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
ctctagggtg aggtctgtcg 20

-continued

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
acactttctt taccacagtg 20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
cagtgtgcct tcccctaacc 20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
tgcaccacag aaattccatg 20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
tctgcctgca ccacagaaat 20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
atgtccactc gctatccgtt 20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
cactcacaat gtccactcgc 20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 147
ttgtagggta gcccgaggcc 20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
cagacctgaa atgccttcca 20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
agcaaagctg acctcagacc 20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
tgcagtgagc aaagctgacc 20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
ctagagcaga tgtactgcag 20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
tccctagagc agatgtactg 20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
caattcccta gagcagatgt 20

<210> SEQ ID NO 154
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 154
acgatatccc aattccctag 20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
aagaaaaatg cttggccgcc 20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
ggcttggtaa actgaagaaa 20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
ggcagtgcaa gatatgattc 20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
gattgtcctt aattccaggc 20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
ttgcagaaag aacggattgt 20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160

-continued atcgaggtga aaagacagtt 20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
tgatgactca tgatgctgat 20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
ctgtgatgac tcatgatgct 20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
gaaactaatt acatgatctg 20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
agttgctggc ccagaaacta 20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
ccccaggcta tgtggactct 20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
tgggaggctc cccggatact 20

<210> SEQ ID NO 167
<211> LENGTH: 20
<212> TYPE: DNA
<213> ORGANISM: Artificial Sequence -continued

```
<220> FEATURE:
<223> OTHER INFORMATION: Antisense Oligonucleotide

<400> SEQUENCE: 167

atttatacaa agattctgag                                                20


<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168

accttaaagt gaggtcttta                                                20
```